United States Patent [19]
Hanna

[11] Patent Number: 6,008,334
[45] Date of Patent: Dec. 28, 1999

[54] BASE-PROTECTED NUCLEOTIDE ANALOGS WITH PROTECTED THIOL GROUPS

[75] Inventor: Michelle M. Hanna, Norman, Okla.

[73] Assignee: The Board of Regents of the University of Oklahoma, Norman, Okla.

[21] Appl. No.: 08/899,022

[22] Filed: Jul. 23, 1997

Related U.S. Application Data

[60] Provisional application No. 60/022,573, Jul. 24, 1996.

[51] Int. Cl.$^6$ .......................... C07H 21/00; C07H 21/02; C07H 21/04
[52] U.S. Cl. ............................. 536/22.1; 435/6; 436/501; 536/23.1; 536/24.1; 536/24.3; 536/24.31; 536/24.32; 536/24.33; 536/25.3; 935/77; 935/78
[58] Field of Search ................................. 536/22.1, 23.1, 536/24.1, 24.3–24.33, 25.3; 435/6; 436/501; 935/77, 78

[56] References Cited

U.S. PATENT DOCUMENTS

4,849,513  7/1989  Smith et al. ............................... 536/27

FOREIGN PATENT DOCUMENTS

0324474  7/1989  European Pat. Off. ..
0371262  6/1990  European Pat. Off. ..
WO 9401445  1/1994  WIPO .

OTHER PUBLICATIONS

Nagamichi et al.; "Synthesis, Chemistry, and Biological Activity of 5–Thiocyanatopyrimidine Nucleosides as Potential Masked Thiols"; *J. Med. Chem.*, 17(4):403–406 (1974).
PF Torrence et al.; "2'–Deoxy–5–(thiocyanato)uridine [1–(2–deoxy–=β–D–crythropentofuranosyl)–5–(thiocyanato)uracil]: Direct Thiocyanation of a Pyrimidine Nucleoside"; *Nucleic Acid Chem*, ed. LB Townsend et al.; Abstract No. 90: 23559m; 1:367–370 (1978).

M. Hanna; "RNA Processing: Photoaffinity Cross–Linking Methods for Studying Protein Interactions", *Methods in Enzymology*, ed. James E. Dahlberg and John N. Abelson; Academic Press, Inc.; 180:383–405 (1989).
M. Hanna et al.; "Synthesis and Characterization of 5–[(4–Azidophenacyl)thio]uridine 5'–Triphosphate, a Cleavable Photo–Cross–Linking Nucleotide Analogue", *Biochemistry*, 28(14):5814–5820 (1989).
Bradley et al.; "Synthesis and Utility of 5–Thiocyanato Deoxyuridine and Uridine Phosphoramidites as Masked Synthons"; *Tetrahedron Letters;* 33(42):6223–6225 (1992).
M. Hanna et al.; "Synthesis and Characterization of a New Photocrosslinking CTP Analog and its Use on Photoaffinity labeling *E. coli* and T7 RNA Polymerases"; *Nucleic Acids Research,* 21(9):2073–2079 (1993).
He et al.; "Preparation of Probe–Modified RNA With 5–mercapto–UTP for Analysis of Protein–RNA Interactions"; *Nucleic Acids Research;* 23(7):1231–1238 (1995).
C.J. Welch et al.; "Synthesid of C–5 and N–3 Arenesulfenyl Uridines. Preparation and Properties of a New Class of Uracil Protecting Group"; *Acta Chemica Scandinavica,* B 39(1985) pp. 203–212. (1985).

*Primary Examiner*—Ardin H. Marschel
*Attorney, Agent, or Firm*—Dunlap & Codding, P.C.

[57] ABSTRACT

The present invention is directed to protected thiol analogs of pyrimidine bases for syntheses of DNA and RNA by chemical or enzymatic methods. The subject analogs include reagents suitable for DNA or RNA synthesis via phosphoramidite, H-phosphonate or phosphotriester chemistry as well a reagents suitable for use by RNA and DNA polymerase, including thermostable polymerases employed by PCR or other nucleic acid amplification techniques. The nucleotide analogs synthesized by methods of this invention can thus be incorporated into oligonucleotides or polynucleotides, deprotected and derivatized with a functional group. In some cases the protecting groups are themselves antigenic and may be left on the oligonucleotides or polynucleotides for detection with antibodies. A method of synthesizing oligonucleotides with a functional group using the subject nucleotide analogs is also provided.

37 Claims, 6 Drawing Sheets

BASE-PROTECTED NUCLEOTIDE ANALOGS WITH PROTECTED THIOL GROUPS

The present application claims the benefit of the filing date of U.S. Provisional Application 60/022,573, filed Jul. 24, 1996.

STATEMENT REGARDING FEDERALLY SPONSORED RESEARCH OR DEVELOPMENT

Not Applicable

BACKGROUND OF THE INVENTION

The present invention is directed to thiol-protected pyrimidine nucleotide analogs which can be used, as one example, for syntheses of DNA and RNA by chemical or enzymatic methods. The subject analogs include reagents suitable for DNA or RNA synthesis via phosphoramidite, H-phosphonate or phosphotriester chemistry as well as reagents suitable for use by RNA and DNA polymerases, including thermostable polymerases employed by PCR or other nucleic acid amplification techniques. Methods of synthesizing the nucleotide analogs are also provided by the present invention. The nucleotide analogs of this invention can thus be incorporated into oligonucleotides or polynucleotides, deprotected, and then derivatized with a functional group.

Oligonucleotides with a variety of modifications have widespread utility for many purposes, such as stabilizing oligonucleotides to degradation, introducing reporter groups, allowing site-specific delivery of therapeutics, and introducing crosslinkers. Such modifications can occur as modified internucleotide phosphate linkages or analogs of such linkages, modified sugars or modified bases. Additionally, 5'- or 3'-end conjugates of the oligonucleotides represent another class of modified oligonucleotides. The present invention relates to base-modified nucleotide analogs with protected thiol groups; these analogs are intermediates for chemical or enzymatic synthesis of oligonucleotides and polynucleotides.

The synthesis of oligoribonucleotides and oligodeoxyribonucleotides (i.e. oligonucleotides) containing base-modified nucleotides at specific positions provides a powerful tool in the analysis of protein-nucleic acid or nucleic acid-nucleic acid interactions. These oligonucleotides have many other potential uses, such as the site-directed delivery of therapeutics, utility as anti-sense therapeutics, and utility as diagnostic probes. Nucleotide analogs can be introduced into nucleic acids either enzymatically, utilizing DNA and RNA polymerases, or chemically, utilizing manual or automated synthesis. Preparation of such oligonucleotides by automated synthesis utilizing, for example, phosphoramidite nucleotides allows for incorporation of a broad range of nucleotide analogs without the restraints for specific substrate conformation of the nucleotides that is imposed by most polymerases. Often, nucleotide analogs containing photoreactive crosslinking groups are introduced into oligonucleotides to probe protein-nucleic acid interactions via photocrosslinking (for a partial review, see Hanna, 1989, *Methods Enzymol.* 180:383–409; and Hanna, 1996, *Methods Enzymol,* 273 Chapter 31). Deoxyoligonucleotides containing 4-thiothymidine have been prepared and used for photochemical crosslinking of proteins directly to the nucleotide bases through the group (Nikiforov et al., 1992, *Nucleic Acids Res.* 20:1209–14). Similarly, oligonucleotides containing 3-(aminopropyl)-2'-deoxyuridine have been prepared and the amino group subsequently modified with fluorescent, photoactive or other reporter groups (Gibson et al., 1987, *Nucleic Acids Res.* 15:6455–66). However, the former thiodeoxynucleotide suffers the disadvantage that if it is modified with a thiol modifying reagent the normal Watson-Crick base of the nucleotide is drastically affected, making this and similar analogs generally unsuitable for use in enzymatic nucleic acid synthesis.

Other analogs involving modifications at the C5 position of deoxyuridine have also been previously reported. The thiol-containing analog, 5-thiocyanatodeoxyuridine phosphoramidite, provided a 5-mercaptodeoxyuridine moiety within the oligonucleotide following reduction of the thiocyanate (Bradley & Hanna, 1992). However, the thiocyanato moiety displayed variable stability during synthesis of both the nucleotide and the oligonucleotide and therefore this compound did not represent an ideal analog for incorporation of 5-thiol modified nucleotides into nucleic acids. The syntheses of a series of phosphoramidites containing alkylthiol tethers at the C5 position of deoxyuridine has been reported (Goodwin & Glick, 1993). The thiol groups in these analogs are attached to the ring by either a three, four, or five carbon chain. The presence of the carbon chains makes the minimal distance between the molecular probes and the oligonucleotide greater than that which can be achieved with our analog. In addition, these compounds represent alkyl thiol analogs which have a lower reactivity for modification of the thiol group than the 5-mercaptopyrimidine analog. This is due to an increase in acidity of 5-mercaptopyrimidines (pKa~5–5.6) over alkylthiol moieties (pKa~8–10). Phosphoramidites containing alkylthiol tethers at the N3 position of thymidine have also been prepared, but the position of this modification results in a disruption of the Watson-Crick base pairing. These analogs have been used mainly for preparing disulfide cross-links in DNA for studies involving stem loop and triple helical structures (Glick, 1991; Goodwin et al., 1994).

Several 5-modified deoxyuridine phosphoramidites are commercially available which contain functional groups (i.e. carboxylic acids or alkyl amines) for post-modification following incorporation into the oligonucleotide. Likewise, alkyl thiol ethers of 5-mercaptodeoxyuridine containing protected carboxylic acids and alkyl amines have also been described (Bergstrom et al., 1991). The protected functional groups in these analogs are not attached directly to the ring but are positioned at the end of carbon chains. These groups are not as easily modified as mercaptans: the functional groups formed during post-synthetic modification are limited, and an easily cleavable group is not available. Thiol-containing phosphoramidites for incorporating 4-thiothymidine (Clivio et al., 1992; Xu et al., 1992c), 4-thiodeoxyuridine (Clivio et al., 1992; Coleman & Kesicki, 1994), 2-thiothymidine (Connolly & Newman, 1989; Kuimelis & Nambiar, 1994), 6-thiodeoxyguanosine (Christopherson & Broom, 1991; Waters & Connolly, 1992; Xu et al., 1992b) and 6-thioinosine (Clivio et al., 1992a) have been reported. These analogs can occupy internal positions within an oligonucleotide and can serve as photochemical crosslinkers. However, they cannot be further modified without disrupting Watson-Crick base pairing, and therefore, as photocrosslinking probes, these analogs are only useful for evaluating interactions which occur directly with the nucleotide base. Modification with other molecular probes (e.g., fluorescent tags) would also disrupt Watson-Crick base pairing. In addition, the deprotection of oligonucleotides containing these thiol-modified nucleotides must be carefully monitored to prevent conversion of these analogs to the corresponding oxygen and nitrogen derivatives.

Described herein are nucleotide analogs which can be used for site-specific modification of DNA or RNA at internal and terminal positions within the DNA or RNA sequence, and after modification, for molecular probes which can be placed at variable distances from the DNA or RNA backbone.

The present invention provides novel base-protected nucleotide analogs, both ribonucleotides and deoxynucleotides, that contain masked thiol groups on the 5 position of pyrimidines, which is not involved in Watson-Crick base pairing. These analogs can be incorporated into oligonucleotides via automated synthesis and isolated with the thiol protecting group intact. After removal of the thiol protecting group many types of functional groups, such as photocrosslinking agents, fluorescent tags, radioisotopes, biotin, reporter molecules, spin labels (e.g., commercially available proxyl or tempo), chemiluminescent, antigenic or other functional groups, can be site-specifically attached by utilizing thiol-modifying reagents. This feature adds a level of specificity to the oligonucleotide modifications not present with the amino-tagged analogs previously described (Gibson et al, 1987), and enables examination of molecular interactions that are not directly at the nucleotide base by allowing functional groups to be placed at varying distances from the base or helix strand. Since these analogs have the functional group attached via the sulfur atom, some have the further advantage of being cleavable under conditions which will not degrade or modify the oligonucleotide.

SUMMARY OF THE INVENTION

This invention relates to pyrimidine nucleotide analogs which contain modified bases with protected thiol groups attached at a position on the base, preferably the 5 position, which is not involved in Watson-Crick base pairing. These nucleotide analogs are intermediates in chemical or enzymatic synthesis of DNA or RNA oligonucleotides and are therefore stable under conditions required for synthesis of these molecules. After synthesis, the protecting group on the analog is removable to generate a reactive thiol group. Once generated, the thiol group can be treated with thiol modifying reagents to attach functional groups such as crosslinking agents or reporter molecules.

In particular, the nucleotide analogs of the present invention have the formula:

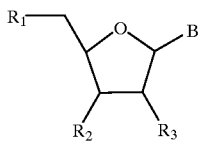

wherein
$R_1$ is —H, —OH, a mono, di, or triphosphate group, or —OR$_4$;
$R_2$ is —H, —OH, a mono, di, or triphosphate group, a phosphoramidite group, a phosphorothioamidite group, a phosphonate group, an O-substituted monophosphate group, —OR$_4$, or a solid support bonded via an O at the 3' position;
$R_3$ is —H, —OH, a mono, di, or triphosphate group, or —OR$_4$;
$R_4$ is a lower alkyl or a protecting group; and
B is a modified pyrimidine base comprising a protected thiol group attached at the 5 position on said base that is not involved in Watson-Crick base pairing or does not disrupt normal Watson-Crick base pairing, said protected thiol group being stable under conditions of chemical nucleic acid synthesis and/or conditions of enzymatic nucleic synthesis and being convertible to a reactive thiol (SH) after said synthesis.

Preferred nucleotide analogs of the present invention are the protected phosphoramidites or 5' mono, di and triphosphates of modified cytosine or uridine bases for use in the chemical synthesis of DNA and RNA by the phosphoramidite method or enzymatic synthesis with polymerases, ligases, or other nucleotide polymerizing enzymes.

In addition, the nucleotide analogs of the present invention include other nucleoside phosphates, containing 3', 5', or 3',5' monophosphates, diphosphates, or triphosphates and further optionally comprising 2' mono, di, or triphosphates when the nucleoside is a ribonucleoside.

Another aspect of this invention provides nucleic acids and oligonucleotides containing the subject nucleotide analogs having a protected thiol group on a base moiety of that nucleic acid or oligonucleotide. A method is also provided to synthesize these nucleic acids or oligonucleotides, deprotect the thiol group and attach a functional group to the reactive thiol moiety.

Yet another aspect of this invention is directed to a method of synthesizing the subject base-protected nucleotide analogs.

DESCRIPTION OF THE DRAWINGS

FIG. 2A. RP HPLC chromatograms of oligonucleotides A and B. The purified 7-mers were analyzed by analytic HPLC on an Ultrasphere ODS column, eluted with a 15 minute linear gradient from 5% to 20% (v/v) acetonitrile in 20 mM TEAA (pH 7.1). (a) Oligonucleotide A, GTA TGT A, eluted at 9.8 min. (b) DNP-labeled oligonucleotide B, GTA T*GT A, eluted at 11.6 min, where T represents incorporation of the DNP-analog described in FIG. 1.

FIG. 2B. RP HPLC profile of enzymatic degradation of oligonucleotides A and B. The 7-mers were subjected to enzymatic treatment with Nuclease P1 and CIP. The reaction mixture was analyzed by analytical HPLC on an Ultrasphere ODS column, eluted with a linear gradient of acetonitrile in 100 mM TEAA (pH 7.1) from 0% to 5% (v/v) in 5 min, 5% to 6% (v/v) in 15 min., 6% to 50% (v/v) in 5 min and finally 50% to 80% (v/v) in 15 min. (a) oligonucleotide A reaction. (b) DNP-labeled oligonucleotide B.

A. PCR products were analyzed by electrophoresis on a 1.5% agarose gel. DNA was detected with ethidium bromide. Lane 1:λ Hind III markers; Lane 2: PCR product using Oligonucleotide E as a primer; Lane 3: PCR product using DNP-labeled Oligonucleotide F as a primer. XC represents xylene cyanol and BPB represents bromophenol blue.

B. Dot Blot immunodetection of DNP-labeled DNA. PCR products were attached to a nylon membrane, incubated with a primary antibody to DNP and a 2° antibody linked to horseradish peroxidase. Chemiluminescence was used for detection. Upper panel: PCR product using DNP-labeled oligonucleotide F as a primer; Lower panel: PCR product using Oligonucleotide E as a primer.

Figure 5:
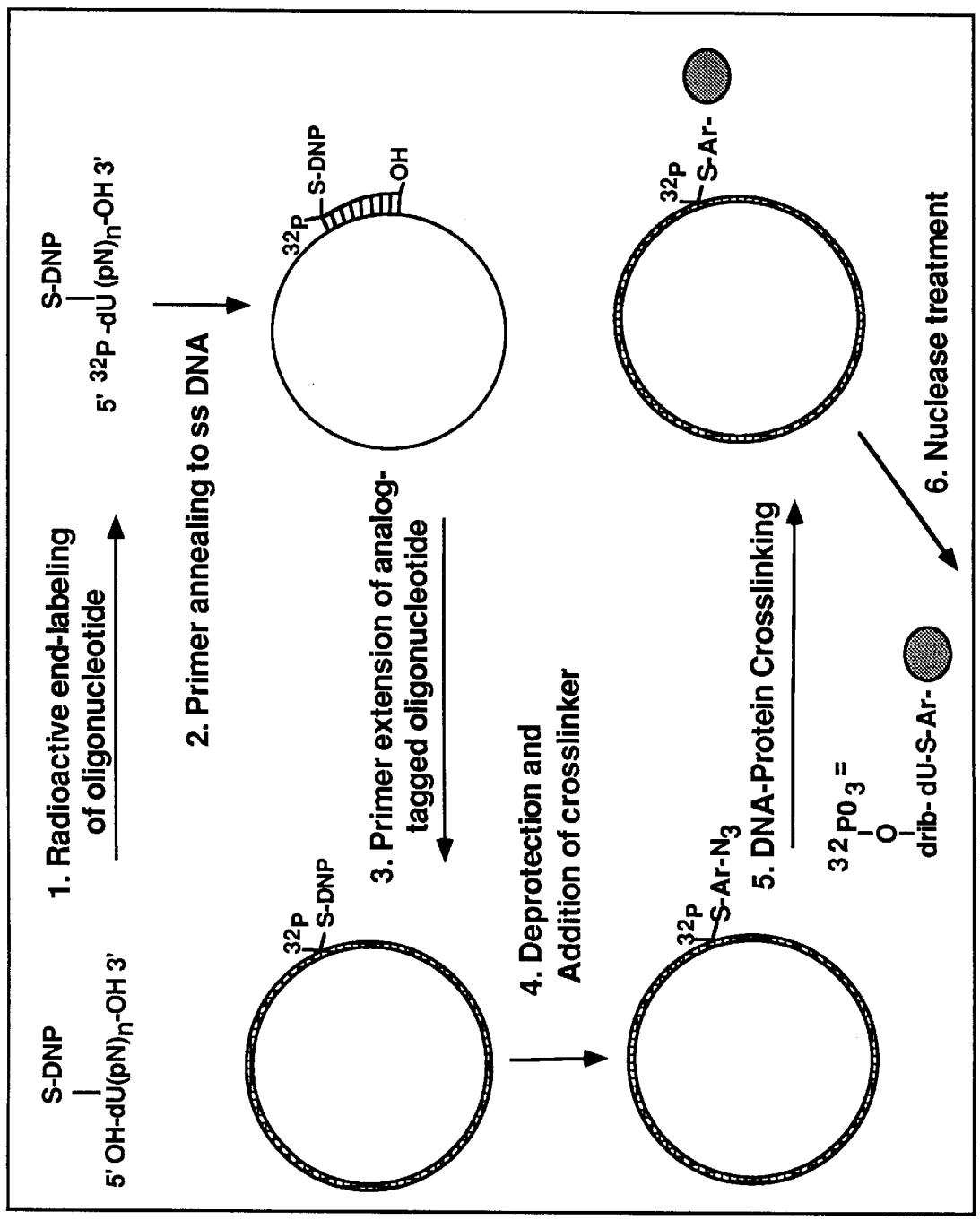

FIG. 5: Protein Crosslinking to Site-Specifically Modified DNA

To analyze the DNA-protein complexes in the transcription complex a deoxynucleoside phosphoramidite was incorporated site-specifically into a single-stranded DNA oliqonucleotide via automated synthesis. In these studies, the nucleotide analog was modified with a masked reactive thiol group on the non-basepairing 5 position of deoxyuridine (5-S-DNP-dU, FIG. 1). The oligonucleotide was then radioactively labeled uniquely on the 5' phosphate of the nucleotide analog with polynucleotide kinase and [γ-$^{32}$P] ATP (Step 1). The radioactively labeled, base-modified oligonucleotide was then annealed to a single-stranded DNA template (Step 2) and incorporated site-specifically into double stranded DNA by primer extension (Step 3). The protecting group was then removed from the double-stranded DNA by treatment with β-mercaptoethanol (Step 4), and after removal of the BME, a functional group was added to the unmasked thiol group. For crosslinking, the DNA was reacted with azidophenacyl bromide to attach a photoreactive azide group (Step 4). RNA polymerase and transcription factors are then added to assemble a complex on the modified DNA, and the complex is irradiated with ultraviolet light to covalently join the DNA to proteins which are bound adjacent to the crosslinker (Step 5). Lastly, the DNA-protein complex is treated with a nuclease which leaves 5' NMPs to digest the DNA to a small fragment (Step 6). This will leave a single radioactive label on the 5' phosphate of the nucleotide involved in the DNA-protein crosslink.

Figure 6:
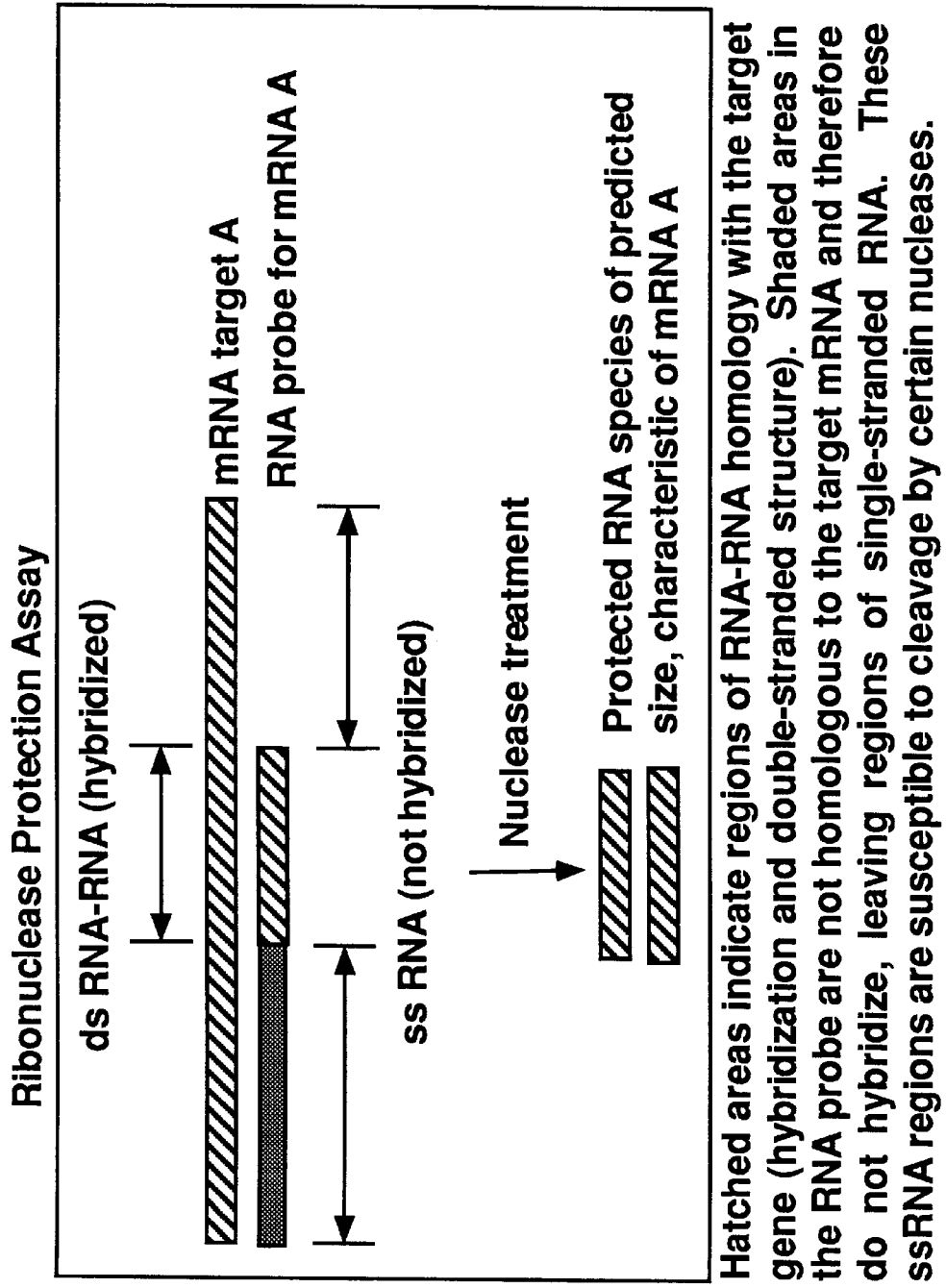

FIG. 6 Hybridized structures are depicted which are involved in a Ribonuclease Protection Assay.

DETAILED DESCRIPTION OF THE INVENTION

The present invention relates to a series of novel nucleotide analogs which are masked synthons for use as intermediates in chemical or enzymatic synthesis of nucleic acids, including synthesis of both oligonucleotides and polynucleotides. The nucleotide analogs of this invention, which contain a protected thiol group, can thus be incorporated into DNA or RNA under standard synthetic conditions without loss of the thiol protecting group. This stability of the thiol protecting group permits site-selective introduction into a nucleic acid of the nucleotide analog in a manner which facilitates later addition of a functional group at that site. Thus, the subject oligonucleotides (or polynucleotides) can contain one (or more) of the subject nucleotide analogs.

Thus, functional groups which can not withstand the conditions for chemical nucleic acid synthesis, especially during automated synthesis, or which may be too bulky or sterically hindered for enzymatic nucleic acid synthesis can be readily incorporated into the final oligonucleotide (or polynucleotide) product. Such derivatized nucleic acids have great utility in studying protein-nucleic acid or nucleic acid-nucleic acid interactions, as well as the potential for diagnostics and delivery of therapeutics. Hence, the present invention permits the skilled artisan to place chemical tags such as crosslinking groups, fluorescent molecules, radioisotopes or other reporter molecules at specific positions on nucleic acid molecules for analysis of molecular mechanisms, for creation of diagnostic probes, for therapeutics, for antisense therapeutics and for many other purposes.

In particular, the nucleotide analogs of the present invention are intermediates for the chemical synthesis of DNA and RNA by manual or automated techniques and are represented by the formula:

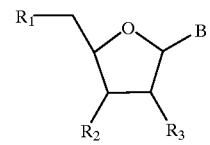

wherein
  $R_1$ is —H, —OH, a mono, di, or triphosphate group, or —$OR_4$;
  $R_2$ is —H, —OH, a mono, di, or triphosphate group, a phosphoramidite group, a phosphorothioamidite group, a phosphonate group, an O-substituted monophosphate group, —$OR_4$, or a solid support bonded via an O at the 3' position;
  $R_3$ is —H, —OH, a mono, di, or triphosphate group, or —$OR_4$;
  $R_4$ is a lower alkyl or a protecting group; and
  B is a modified pyrimidine base comprising a protected thiol group attached at a position on said base, preferably the 5 position, that is not involved in Watson-Crick base pairing or does not disrupt normal Watson-Crick base pairing, said protected thiol group being stable under conditions of chemical nucleic acid synthesis and/or conditions of enzymatic nucleic synthesis and being convertible to a reactive thiol after said synthesis.

As used herein, protecting groups defined by $R_4$ are known to those of ordinary skill in the art and include any known protecting group suitable for protection of the 2', 3' or 5' hydroxyls of ribose and the 3' or 5' hydroxyls of deoxyribose sugars. In this regard, Greene et al. (1990) *Protecting Groups in Organic Synthesis*, 2nd ed., John Wiley & Sons, Inc., New York, N.Y., provides a comprehensive review of protecting groups, and methods of preparing the corresponding protected compounds, which can be used for different reactive groups, including reactive hydroxyl groups.

Accordingly, examples of protecting groups defined by $R_1$, $R_2$ and $R_4$ are lower alkyl, lower cyanoalkyl, lower alkanoyl, aroyl, aryloxy, aryloxy-lower alkanoyl, haloaryl, fluorenylmethyloxycarbonyl (FMOC), levuloyl, 9-phenylxanthene-9-yl, trityl, p-monomethoxytrityl (MMTr), p-dimethoxytrityl (DMTr), isopropyl, isobutyl, 2-cyanoethyl, acetyl, benzoyl, phenoxyacotyl, halophenyl, 1-(2-chloro-4-methylphenyl)-4-methoxy-4-piperidinyl, 2'-acetal, O-nitrobenzyl, tert-butyldimethylsilyl (TBDMS), tetrahydrofuranyl, 4-methoxytetrahydropyranyl and related groups.

Preferred $R_1$ protecting groups include 5' OH protecting groups especially DMTr, MMTr, FMOC, levuloyl and 9-phenylxanthene-9-yl groups, and most preferably DMTr. Preferred $R_2$ protecting groups include 3' OH protecting groups, especially the acetyl group. Preferred $R_4$ protecting groups include 2' OH protecting groups, especially 2'-acetal, tetrahydrofuranyl, 4-methoxytetrahydropyranyl and 1-(2-chloro-4-methylphenyl)-4-methoxy-4-piperdinyl groups, and most preferably TBDMS.

As defined herein, solid supports include controlled pore glass (CPG), polystyrene silica, cellulose, nylon, and the like. Preferred solid supports are CPG and polystyrene. An especially preferred solid support is CPG.

$R_2$ can be taken with the oxygen atom to which it is attached, to form a phosphoramidite, phosphorothioamidite, a phosphonate, an O-substituted monophosphate, or any other group compatible with chemical nucleic acid synthesis, especially automated DNA or RNA synthesis. As used herein, the phosphoramidite and phosphorothioamidite groups have the general formulas I and II, respectively:

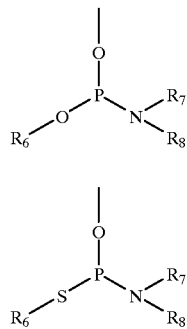

wherein $R_6$ is lower alkyl, n-cyano alkyl, substituted lower alkyl, aryl, aralkyl, substituted aralkyl and the like, and $R_7$ and $R_8$ are independently lower alkyl or when taken together with the nitrogen to which they are attached comprise cyclic groups including:

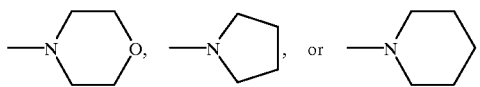

preferably the $R_6$ group of the phosphoramidite group (Formula I) is 2-cyanoethyl (CED) or methyl. Accordingly, the preferred phosphoramidites of this invention are also referred to as CED phosphoramidites or methyl phosphoramidites.

As used herein, the term lower alkyl, when used singly or in combination, refers to alkyl groups containing one to six carbon atoms. Lower alkyl groups can be straight chain or branched and include such groups as methyl, ethyl, propyl, isopropyl, n-butyl, sec-butyl, isobutyl, t-butyl, pentyl, isopentyl, neopentyl, hexyl and the like. The preferred alkyl groups contain one to four carbon atoms.

The term aryl, when used alone or in combination, refers to an aromatic ring containing six to ten ring carbon atoms. The aryl group includes phenyl, and 1- or 2-naphthyl. The preferred aryl group is phenyl.

The term aralkyl refers to aryl groups as described above to which substituents are attached to the aryl by an alkylene bridge. The most preferred aralkyl group is benzyl.

When $R_7$ and $R_8$ are lower alkyl, the preferred groups are each isopropyl groups.

As used herein a phosphonate group (or H-phosphonate) is represented by the formula:

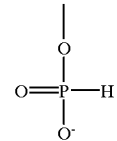

and may also be provided as salts, and preferably as triethylammonium salts.

As used herein, O-substituted monophosphates have the formula:

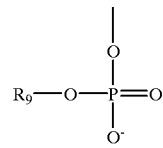

wherein $R_9$ is lower alkyl, haloalkyl, aryl, haloaryl, or heteroaromatic. By haloalkyl or haloaryl is meant alkyl or aryl groups, respectively, which have been substituted with one or more halogen atoms including F, Cl, Br, or I. Preferred halo substituents are Cl and Br. Preferred $R_9$ groups include 2-chlorophenyl, 2,5-dichlorophenyl, 2,2,2-trichloroethyl and the N-oxide of 4-methoxypyridine-2-methylene groups.

Modified pyrimidine bases have a protected thiol group attached at a position on the base which is not involved with Watson-Crick base pairing or which does not disrupt normal Watson-Crick base pairing. The protected thiol groups of this invention are stable, i.e. not removable, under the conditions used for chemical synthesis of DNA or RNA, and particularly, under the conditions employed in automated DNA or RNA synthesis. Furthermore, the protecting group of the thiol is removable under conditions which do not disrupt the integrity of the oligonucleotide or polynucleotide. In other words, after a nucleotide analog of the present invention has been incorporated into an oligonucleotide, for example, the protected thiol group can be converted to a reactive thiol (SH) to which functional groups can subsequently be added using thiol-modifying reagents.

In accordance with this invention the protected thiol groups include, but are not limited to, the dinitrophenyl group. As used herein, Watson-Crick base pairing refers to the hydrogen bonding pattern of adenine-thymine (AT) base pairs, adenine-uracil (AU) base pairs, or of gtianine-cytosine (GC) base pairs. Accordingly, the preferred protected thiol position on pyrimidines is the 5 position on the pyrimidine (C,U) ring.

The preferred bases of the present invention are thus pyrimidines such as cytosine (C), and uracil (U). Cytosine bases contain an additional reactive group, specifically an exocyclic amine, which must also be protected during assembly of the nucleotide chain via chemical synthesis. Accordingly, bases of this invention can have additional protecting groups attached as needed to any of the ring positions. Such protected bases are well known in the art and include but are not limited to, $N^2$, $N^4$-anisoyl cytosine, $N^4$-benzoyl cytosine, and $N^4$-isobutyryl cytosine. The $N^4$-isobutyryl cytosine is known by the trade name FOD™ base protection (Applied Biosystems, Inc.). Use of these further protected bases is compatible with incorporation of the protected thiol groups as well as subsequent deprotection reactions.

The bases of this invention also include any related base analog that is capable of base pairing with a guanine or adenine, the corresponding protected analogs as set forth above for use in chemical synthetic methods to produce DNA and RNA. For example, such base analogs include, but are not limited to, pseudocytosine, isopseudocytosine, 4-acetylcytosine, 2'-O-methylcytosine, dihydrouracil, 2'-O-methyluracil, 2'-O-methyl-pseudouracil, 1-methylpseudouracil, 3-methylcytosine. Bases attached to a ribose or deoxyribose sugar in an α-anomeric configuration can also be present.

In a preferred embodiment the bases of the invention are C, U, and $N^4$ protected C.

The compounds of the present invention also include nucleoside phosphates of the formula:

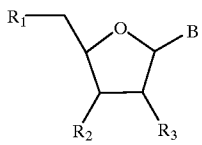

wherein:

$R_1$ is —H, —OH, a mono, di, or triphosphate group, or —$OR_4$;

$R_2$ is —H, —OH, a mono, di, or triphosphate group, a phosphoramidite group, a phosphorothioamidite group, a phosphonate group, an O-substituted monophosphate group, —$OR_4$, or a solid support bonded via an O at the 3' position;

$R_3$ is —H, —OH, a mono, di, or triphosphate group, or —$OR_4$;

$R_4$ is a lower alkyl or a protecting group; and

B is a modified pyrimidine base comprising a protected thiol group attached at the 5 position on said base.

In the case of the modified bases the protected thiol group is also stable, i.e. not removable, under the conditions used for enzymatic synthesis of DNA or RNA. Additionally, the pyrimidine bases generally do not require protection of the additional reactive groups such as the exocyclic amines for enzymatic incorporation into DNA or RNA. Accordingly, the preferred bases for this class of compounds includes C and U.

In accordance with this invention the phosphate groups of $R_1$, $R_2$ and $R_3$ embody all the phosphorylated forms at the $C_3'$ and $C_5'$ positions of the sugar moiety (and $C_2'$ position when the sugar is ribose) and include monophosphates, diphosphates, triphosphates and tetraphosphates. Preferably the phosphate group is a triphosphate for $R_1$.

The preferred compounds of this invention include the phosphoramidites and 5' triphosphates of 5-SDNP-dU, 5-SDNP-U, 5-DNP-dC, and 5-DNP-C. In the case of the phosphoramidites, the base moieties can contain additional protecting groups on the exocyclic amines. The preferred compounds also include the 5' triphosphates of 5-S-S-Et-dU, 5-S-S-Et-U, 5-S-S-Et-dC and 5-S-S-Et-C, 5-S-CH$_2$-NHCOCH$_2$Ph-dU, 5-S-CH$_2$—NHCOCH$_2$Ph-U, 5-S-CH$_2$—NHCOCH$_2$Ph-C, 5-S-CH$_2$—NHCOCH$_2$Ph-dC, 5-SCH$_2$CH$_2$DNP-dU, 5-SCH$_2$CH$_2$DNP-U, 5-SCH$_2$CH$_2$DNP-dC, and 5-SCH$_2$CH$_2$DNP-C.

The nucleotide analogs of the present invention can be prepared by adding a protected thiol group to the base moiety of the desired nucleoside. The so-modified nucleoside can then be phosphorylated to produce a nucleotide analog phosphate compound of this invention using conventional phosphorylation techniques. To produce a phosphoramidite, phosphonate, phosphorothioamidite or O-substituted monophosphate of this invention, the 5'—OH or 2'-OH groups of above-modified nucleoside are protected as necessary by addition of the desired protecting group by standard methodology. This protection step(s) is (are) followed by conversion to the nucleotide-analog phosphoramidite, phosphorothioamidite, phosphonate or O-substituted monophosphate by reaction of the 3'OH of the nucleoside with the appropriate modifying group. Similarly, the 3'OH can be attached to a solid support, such as CPG, or another protecting group using conventional methodology available to the ordinarily skilled artisan in this field.

For example, to prepare protected thiol-groups at the 5 position of uridine or 2'-deoxyuridine nucleosides, the sulfur atom must be incorporated on the base, for which the method of Nagamchi et al. (1972, *J.C.S. Chem. Commun.* 18:1025–6) has been modified. An equivalent amount of potassium thiocyanate is dissolved into a solution of chlorine gas in glacial acetic acid to produce the thiocyanogen chloride in solution. An iodometric titration is performed with Cl$_2$/HOAc to determine the amount of Cl$_2$ present. The solution can be used directly or filtered prior to the next step. In either case, the acetyl-protected U or dU is added all at once with stirring. This reaction is maintained with stirring at room temperature for about 1.5 hours until the reaction is completed. An excess of cyclohexene or other quenching agent is then added to quench any remaining thiocyanogen chloride. Quenching is complete in 15 to 60 min, and usually in about 30 min. After removing solvents and organic residue in vacuo, the remaining residue can be purified by silica gel chromatography with a gradient of petroleum ether and ethyl acetate or with other chromatographic methods. These acetyl-protected 5-thiocyanato dU and U nucleosides can then be reduced to 5-mercapto nucleosides for further derivatization as described herein to produce the nucleotide analogs of the present invention.

The mono-, di-, tri or tetra phosphate compounds can be prepared by a similar reaction by beginning with the appropriate starting 5-thioprotected nucleoside. If necessary, the 2'-OH of the ribose sugar can be protected prior to the reaction using any of the known 2'-OH protecting groups by conventional techniques.

The described synthesis and utilization of 5-thiocyanatodeoxyuridine phosphoramidite for placement of the sulfur directly on the base has been previously described (Bradley & Hanna, 1992). However, the synthesis of 5'-O-(4,4'-dimethoxytrityl)-5-S-(2,4-dinitrophenyl) mercapto-2'-deoxyuridine-3'-O-(2-cyanoethyl-N,N'-diisopropyl) phosphoramidite is more reproducible and the product is more stable than 5-thiocyanatodeoxyuridine phosphoramidite and represents a more desirable analog. A variety of functional groups can be attached to the reactive thiol. Once this modified nucleotide is incorporated into an oligonucleotide or nucleic acid, the protecting group can be removed to unmask the reactive thiol, making it available for further derivitization with thiol-specific agents. This method has the advantage that an oligonucleotide tagged with this analog can be synthesized and stored for long periods without removal of the protecting group. When needed, an aliquot can then be deprotected and modified. In addition, in some cases the protecting groups are themselves antigenic (e.g., ⁻DNP) and may be retained in the nucleic acid product for detection utilizing antibodies.

Figure 1:
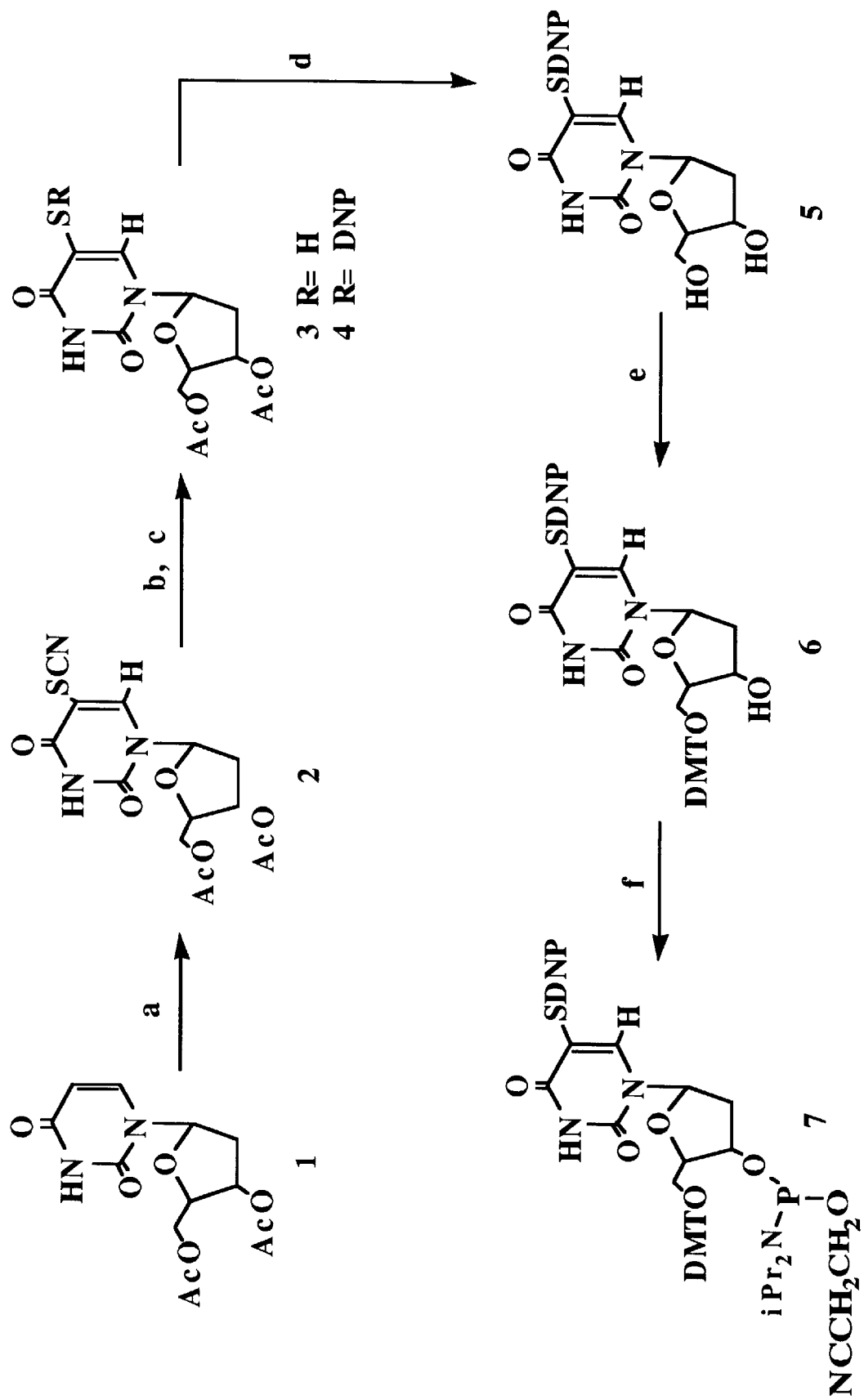
FIG. 1: Synthetic pathway for the DNP-labeled phosphoramidite (compound 7). Reaction conditions are as follows a) SCNCl, CH$_3$CO$_2$H; b) DTT,MeOH,EDTA; c) 2,4-dinitrofluorobenzene, Et$_3$N,CH$_3$CN; d) NaOMe,MeOH; e) DMT$^+$BF$^-_4$,DBMP,CH$_3$CN; f) 2-cyanoethyl-N, N, N', N'-tetraisopropyl-phosphorodiamidite, tetrazole, CH$_3$CN.

One method used to produce one of the nucleotide analog phosphoramidites of this invention and described in detail in Example 1 below is shown in FIG. 1. Briefly, as depicted, 5-SDNP-dU or 5-SDNP-U are prepared by reduction of the SCN, protection of the thiol as the DNP ether, and de-esterification of the sugar ring. The protected-thiol nucleoside thus formed is then reacted with the $DMT^+BF_4^-$, or another 5'OH protecting group, in an anhydrous organic solvent in the presence of an organic base for 2–24 hours until the reaction is complete. The resulting product can be isolated by liquid chromatographic methods and then converted to a CED phosphoramidite by reaction with 2-cyanoethyl N, N, N', N'-tetraisopropyl phosphordiamidite and tetrazole under anhydrous conditions and in an inert atmosphere. This reaction is preferably stirred for 1 hour, although this time can be varied, the solvents removed in vacuo and the residue purified by chromatographic methods. Exposure to atmosphere is acceptable but should be minimized. This phosphoramidite can be stored dry under positive pressure of inert atmosphere (argon or nitrogen) in a tightly sealed container at low temperature.

Other phosphoramidites of this invention can be prepared by reaction with the appropriate chlorophosphoroamidite. For example, the O-methylphosphoramidites can be prepared by reacting the 5-SDNP-5'-DMTr-dU with N,N-diisopropylmethylphosphonamidic chloride by conventional techniques. Similarly, the phosphorothioamidite, phosphonates, O-substituted monophosphate can be prepared using conventional techniques with commercially available reagents. As mentioned above to avoid unwanted side reactions, protection of the 5'OH and 2'OH groups on the sugar moiety and the exocyclic amine groups on the base moiety may be necessary before the final reaction step which produces the nucleotide analogs of this invention.

In general the chemical synthetic routes to nucleotide phosphoramidites, phosphorothioamidites, phosphonates and O-substituted monophosphates, as well as nucleotide phosphates, are well known. In addition, nucleoside phosphates can be enzymatically synthesized. Chemical synthetic techniques for these compounds, as well as the common synthetic routes to prepare RNA and DNA, have been described in many sources. Particularly, useful references include Gait (1984) *Oligonucleotide Synthesis: A Practical Approach*, IRL Press, Oxford; Blackburn et al. (1990) *Nucleic Acids in Chemistry and Biology*, IRL Press, Oxford, especially Chap. 3; Chaps 13–16 of *Methods in Enzymology*, Vol. 154 (Wu et al., eds.) Academic Press, San Diego, Calif., 1987; Chaps. 13–14 in *Methods in Molecular Biology*, Vol. 4 (Walker, ed.), Humana Press, Clifton, N.J., 1988; and Uhlmann et al. (1990) *Chem. Rev.* 90:544–584.

In addition to providing methods for chemical synthesis of DNA and RNA, some of these references (particularly Gait and Uhlmann et al.) describe the reactions and methodology for adding protecting groups to 5'OH, 3'OH and 2'OH groups, and exocyclic amine groups ($N^6$ of adenine, $N^4$ of cytosine, $N^2$ of guanine). These references also provide information and protocols to attach nucleotides to solid supports which protocols are useful for attaching the base-protected nucleotide analogs of this invention.

The synthesis of 5-SDNP-dC and 5-SDNP-C can be accomplished by reaction of 5-Br-dC or 5-Br-C with sodium hydrogen sulfide, as described by Solan, followed by conversion into the DNP thiol ether. In these cases, it may be necessary to first protect the 4 amino group of cytosine (e.g., as the iso-butoxy amide) and complete the remaining protection steps (5'-O-DMTr and 2'-O-TBDMS, if needed) before preparation of a CED phosphoramidite or conversion to the triphosphate (Sung, 1982, *J. Org. Chem.* 47:3623). Alternatively, 5-S-dU or 5-S-U can be converted to the corresponding compounds. Several methods are available for this conversion of U to C, including Sung, Xu, and MacMillan.

The conversion of 5-SDNP-dU and 5-SDNP-U to 5' phosphates, phosphoramidites, phosphorothioamidites, phosphonates, and O-substituted monophosphates has been described herein above. All of these reaction schemes can be used to produce the corresponding thiol protected cytosine analogs. If necessary, various protecting groups for the 5'OH, 3'OH or 2'OH groups as well as the exocyclic amines can be added in accordance with the methodology described herein.

Another aspect of this invention relates to the oligonucleotides or polynucleotides containing the nucleotide analogs of this invention and a method of preparing such nucleic acids using the subject nucleotide analogs. oligonucleotides and polynucleotides of this invention are made by standard methods of chemical (automated or manual) synthesis or enzymatic synthesis of DNA and RNA. Such methods are well known in the art. In chemical synthesis, the nucleotide analog of this invention is substituted for a particular nucleotide at the desired point in the synthesis.

After incorporation of the nucleotide analog and complete synthesis of the oligonucleotide or polynucleotide, the thiol can be deprotected and reacted with any number of thiol-modifying reagents to attach a functional group at that point on the oligonucleotide or polynucleotide. Deprotection of S-DNP or S-S-Et can be accomplished by treatment with β-mercaptoethanol or by other means of reducing sulfides. In a preferred method for the DNP analog, deprotection is accomplished by treating the oligonucleotide with 1.4M BME at 45° C. for 4 hours or at room temperature overnight.

Any variety of functional groups can then be added to the reactive thiols group generated by the deprotection step. Such functional groups include cross-linking groups, photoactive cross-linking groups (e.g. arylazides), and reporter molecules such as radioisotopes, biotin, enzymes and fluorescent markers. The methods for adding functional groups are well know in the art.

Yet another aspect of this invention provides a method of preparing the nucleotide analogs of the invention. In particular, this method involves preparing a thiol protected nucleoside or nucleotide base wherein said thiol is attached to a position on said base that is not involved in Watson-Crick base pairing or does not disrupt normal Watson-Crick base pairing; reacting said nucleoside or nucleotide base under conditions to effect conversion of said base to a phosphoramidite, phosphorothioamidite, phosphonate, O-substituted monophosphate or phosphate nucleotide analog and under conditions which do not destroy the protected thiol; and recovering said analog. In accordance with this invention, this method is accomplished as described above for synthesis of the subject nucleotide analogs. Recovery of the analogs can be accomplished by HPLC, FPLC or other chromatographic separation techniques.

A further aspect of this invention provides a method of synthesizing a nucleic acid with a functional group by incorporating a thiol protected nucleotide analog in accordance with this invention into a nucleic acid by a chemical or enzymatic method for nucleic acid synthesis; recovering the nucleic acid containing the analog; deprotecting the analog of that nucleic acid to produce a nucleic acid containing a reactive thiol group; reacting the reactive thiol group with a thiol-modifying reagent to thereby attach a functional group and produce the nucleic acid with the functional group; and recovering the nucleic acid with the functional group. In accordance with this invention, this method is accomplished as described hereinabove for synthesis of oligonucleotides and polynucleotides (See for example Gait or Sambrook et al). As used herein, nucleic acids include oligonucleotides and polynucleotides. Preferably, the oligonucleotides range in size from about 5 to about 100 nucleotides. Polynucleotides range in size from 100 nucleotides to 10 kb or more. Recovery of the analogs can be accomplished by HPLC, FPLC, other chromatographic techniques, extraction, phase separation or precipitation.

While the invention will now be described in connection with certain preferred embodiments in the following examples so that aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus the following examples, which include preferred embodiments, will serve to illustrate the practice of this invention, it being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the invention.

EXAMPLES

Procedures

Materials. Unless otherwise stated, starting materials for the chemical synthesis of the phosphoramidite were obtained from Aldrich, Sigma, Fluka or Fisher Scientific and were used without further purification. Anhydrous HOAc was prepared by fractional freezing (Nagamachi et al., 1974). Anhydrous $CH_2Cl_2$ was distilled from phosphorus pentoxide. Anhydrous $CH_3CN$ was purchased from Cruachem. Dowex 50W x4 was purchased from BioRad. Analytical thin layer chromatography was performed on Whatman silica gel 60 plates with fluorescent indicator. Column chromatography was performed with silica gel 60A from American Scientific Products. Reagents for the oligonucleotide syntheses were obtained from Cruachem. Standard exocyclic amine protecting groups were used: Benzoyl for dA and dC and isobutyryl for dG. Solvents utilized for the reverse phase chromatographic purification of the oligonucleotides were of HPLC grade. The fluorescent thiol modifying agent, 5-IAF was purchased from Molecular Probes (Eugene, Oreg.).

Buffers. The buffers used were as follows: buffer A, 100 mM TEAA (pH 7.1); buffer B, 20 mM TEAA (pH 7.1); buffer C, 50 mM Tris-HCl (pH 4.9), 1 mM $MgCl_2$, 0.1 mM $ZnCl_2$; buffer D, 50 mM Tris-HCl (pH 9.0), 1 mM $MgCl_2$, 0.1 mM $ZnCl_2$, 0.5 mM spermidine; buffer E, 7 M urea, 0.05% (w/v) xylene cyanol; buffer F, 5% (v/v) glycerol, 0.04% (w/v) xylene cyanol, 0.04% (w/v) bromophenol blue.

Enzymes and Antibodies. Nuclease P1 was obtained from Pharmacia Biotech. CIP was supplied by Promega. T4 Polynucleotide Kinase was purchased from New England Biolabs. AmpliTaq Polymerase was obtained from Perkin Elmer. Rabbit polyclonal anti-DNP antibody was purchased from Sigma. Anti-rabbit Ig, horseradish peroxidase-linked whole antibody was obtained from Amersham.

Analytical Methods. Melting points were determined on a Mel-Temp melting point apparatus and are uncorrected. $^1H$ NMR and $^{31}P$ NMR spectra were recorded on a Varian XL-300 or 500 spectrometer, respectively. Chemical shifts are reported in parts per million (δ) relative to internal tetramethylsilane or to external 85% phosphoric acid. UV spectra were measured on either a LKB Biochem Ultraspec II or a Beckman DU 7500 spectrophotometer. IR spectra were recorded with a Perkin Elmer 710B Infrared spectrometer. FAB MS were recorded on a VG analytical ZAB-E spectrometer. Unless otherwise stated, all chemical reactions were performed under a nitrogen atmosphere.

HPLC analyses were performed with a Beckman LC system which was equipped with a 126 solvent delivery module and a 168 diode array detector and was controlled with Beckman System Gold Software. A reverse phase C18 column (Beckman Ultrasphere ODS, 250×4.6 mm, i.d.) and guard column (Upchurch, 1 cm×4.3 mm, i.d.) were utilized with both analytical and semi-preparative separations. Sample loops of 1 mL and 50 μL were used for semi-preparative and analytical analyses, respectively. All HPLC analyses were performed using a gradient solvent system composed of triethylammonium buffers and acetonitrile at a flow rate of 1 mL/min. Unless otherwise stated, UV absorption was monitored at a wavelength of 260 nm.

Abbreviations: DNP,2,4-dinitrophenyl; 5-IAF, 5-iodoacetamidofluorescein; CIP, Calf intestinal alkaline phosphatase; TEAA, triethylammonium acetate; TEAB, triethylammonium bicarbonate; DMT, dimethoxytrityl; RP HPLC, reverse phase high pressure liquid chromatography; PCR, polymerase chain reaction; DTT, dithiothreitol; EDTA, ethylenediaminetetraacetic acid; DMTCl, dimethoxytrityl chloride; $DMT^+BF^-_4$, dimethoxytrityl tetrafluoroborate; BME, β-mercaptoethanol; HR FAB MS, high resolution fast atom bombardment mass spectroscopy.

Example 1

Preparation of 5-SDNP-dU-phosphoramidite

Shown in FIG. 1 and described in detail below is the pathway used for the synthesis of the DNP-labeled phosphoramidite, Compound 7.

Synthesis of 3',5'-O-Diacetyl-5-thiocyanato-2'-deoxyuridine (Compound 2).

Anhydrous HOAc (150 mL) was added to a three-neck round bottom flask equipped with a vacuum adapter and teflon needle. Dry $Cl_2$ was slowly bubbled through the teflon needle into the reaction vessel for a brief period. A 5 mL aliquot of the $Cl_2$/HOAc solution was removed and subjected to iodometric titration to determine the amount of $Cl_2$ added (2.9 g, 41 mmol) (Flaschka et al., 1969). KSCN, previously dried overnight at 100° C., (4.4 g, 45 mmol) was added to the reaction vessel. The reaction mixture was allowed to stir at room temperature for 30 min. prior to the addition of 3',5'-O-diacetyl-2'-deoxyuridine,3',5'-O-Diacetyl-2'-deoxyuridine was prepared by reaction of deoxyuridine with acetic anhydride in pyridine for an 82% yield: mp=106–108° C. (Lin & Gao, 1983) (1.1 g, 3.5 mmol). After the mixture was stirred for an additional 1.5 hours, cyclohexene (10 mL) was added. The mixture was then stirred for 15 min. and filtered; the filtrate was concentrated under vacuum. Residual HOAc was removed azeo-tropically with toluene and the residue was triturated with petroleum ether. The petroleum ether was decanted and the residue subjected to column chromatographic purification [petroleum ether:EtOAc(2:1–1:3)] which yielded a semi-solid. Recrystallization from EtOH:EtOAc provided Compound 2 as a white solid (1.05 g; 82%):mp 154–156° C.; IR(KBr) 2140 cm$^{-1}$ (SCN stretch); $^1H$ NMR (CDCl$_3$) δ 9.12(bs, 1H, N$_3$H), 8.18

(s, 1H, H$_6$), 6.14 (dd, J=7.8, 5.7 Hz, 1H, H$_{1'}$), 5.13 (m, 1H, H$_{3'}$), 4.24 (m, 1H, H$_{5'}$), 4.19–4.15 (m, 2H, H$_{4'}$ and H$_{5'}$), 2.32 (ddd, J=14.4, 5.7, 2.1 Hz, 1H, H$_{2'}$), 2.13–2.07 (m, 7H, 2 CH$_3$ and H$_{2'}$); UV (MeOH) 270 nm.

Synthesis of 3',5'-O-Diacetyl-5-mercapto-2'-deoxyuridine, (Compound 3).

This reaction should be performed in a fume hood. EDTA (25 mL; 0.1 M, pH 7.7) and DTT (293 mg, 1.90 mmol) were added to a solution of thiocyanate 2 (207 mg, 0.561 mmol) in MeOH (30 mL). The reaction mixture was allowed to stir at room temperature for 35 min. and was then filtered. The filtrate was reduced to half by rotary evaporation, made acidic with 10% (v/v) H$_2$SO$_4$ and extracted with CH$_2$Cl$_2$. The CH$_2$Cl$_2$ extract was concentrated under reduced pressure and the residue was triturated with H$_2$O to provide Compound 3 as a white solid (148 mg; 77%). TLC analysis showed a yellow spot upon development with 2,2'-dithiobis (5-nitropyridine) (Grassetti & Murray, 1969): mp=159–163° C.; IR(KBr) 2530 cm$^{-1}$ (SH stretch); $^1$H NMR (CDCl$_3$) δ 8.70 (bs, 1H, N$_3$H), 7.67 (s, 1H, H$_6$), 6.30 (dd, J=8.2, 5.8 Hz, 1H, H$_{1'}$), 5.22 (m, 1H, H$_{3'}$), 4.43–4.25 (m, 3H, H$_4$, and H$_{5'}$), 3.60 (s, 1H, SH), 2.50 (ddd, J=14.4, 5.8, 2.2 Hz, 1H, H$_{2'}$), 2.21–2.10 (m, 7H, 2 CH$_3$ and H$_{2'}$); UV (0.1 M EDTA w/DTT, pH 7.76) 260, 334 nm. (The broad melting point range may indicate the presence of 5,5"-dithiobis(3',5'-diacetyldeoxyuridine). On the average, 7% disulfide analog was present in the sample as determined by UV absorbance (λmax 335 nm) in the presence and absence of DTT (Bardos & Kalman, 1966)).

Synthesis of 3',5'-O-Diacetyl-5-S-(2,4-dinitrophenyl) mercapto-2'-deoxyuridine, (Compound 4).

2,4-Dinitrofluorobenzene (57 mg, 0.31 mmol) and Et$_3$N (200 μL) were added to a solution of mercaptan 3 (86 mg, 0.25 mmol) in anhydrous CH$_3$CN (10 mL). The reaction mixture was allowed to stir at room temperature for 1.5 hours before the solvent was removed by rotary evaporation. The crude material was purified using column chromatography [Hexanes: EtOAc(4:1 to 1:1)]. The product was obtained as a yellow solid (113 mg, 89%): IR(KBr) 1530, 1340 cm$^{-1}$ (NO$_2$ stretch); $^1$H NMR (CDCl$_3$) δ 9.14 (d,J=2.4 Hz, 1H, H$_3$ of DNP), 8.40 (bs, 1H, N$_3$H), 8.31 (dd, J=9.1, 2.5 Hz, 1H, H$_5$, of DNP), 8.23 (s, 1H, H$_6$), 7.33 (d,J=9 Hz, 1H, H$_6$ of DNP), 6.32 (dd, J=7.8, 5.7 Hz, 1H, H1'), 5.25, (m, 1H, H$_{3'}$), 4.44–4.25 (m, 3H, H$_4$, and H$_{5'}$), 2.55 (m, 1H, H$_{2'}$), 2.27 (m, 1H, H$_{2'}$), 2.13 (s, 3H, CH$_3$), 2.10 (s, 3H, CH$_3$); UV (MeOH) 264, 323 nm.

Synthesis of 5-S-(2,4-Dinitrophenyl)mercapto-2'-deoxyuridine, (Compound 5).

NaOMe (25% solution in MeOH; 82 μL; 0.36 mmol) was added to a solution of Compound 4 (92 mg, 0.18 mmol) in anhydrous MeOH (6 mL) and the reaction mixture was maintained at room temperature. After 2 hours, the mixture was treated with Dowex 50W ×4 and filtered. The filtrate was reduced by rotary evaporation. The product was obtained as a yellow solid following column chromatographic purification of the reaction mixture [EtOAc: petroleum ether (1:4 to 1:0)] (62 mg; 81%): IR(KBr) 1530, 1340 cm$^{-1}$ (NO$_2$ stretch); $^1$H NMR (Cd$_3$OD) δ 9.08 (d, J=2.4 Hz, 1H, H$_3$ of DNP), 8.85 (s, 1H, H$_6$), 8.39 (dd, J=9, 2.4 Hz, 1H, H$_5$ of DNP), 7.64 (d, J=9 Hz, 1H, H$_6$ of DNP), 6.33 (t, J=6.3 Hz, 1H, H$_{1'}$), 4.45 (m, 1H, H$_{3'}$), 4.00 (m, 1H, H$_{4'}$), 3.84 (dd, J=12, 3 Hz, 1H, H$_{5'}$), 3.75 (dd, J=12, 3 Hz, 1H, H$_{5'}$), 2.50–2.33 (m, 2H, H$_{2'}$); UV (0.1 M TEAA, pH 7.1 with 57% CH$_3$CN) 262, 334 nm.

Synthesis of 5'-O-Dimethoxytrityl-5-S-(2,4-dinitrophenyl) mercapto-2'-deoxyuridine (Compound 6).

Anhydrous CH$_3$CN (6 mL) was added to a mixture of compound 5 (42 mg, 0.10 mmol), DMT$^+$BF$_4^-$(57 mg, 0.14 mmol) and 2,6-di-tert-butyl-4-methylpyridine (DBMP) (35 mg, 0.18 mmol). The resulting red solution was heated to reflux. After 1.5 hours, a second portion of DMT$^+$BF$_4^-$—(26 mg, 0.064 mmol) and DBMP (13 mg, 0.067 mmol) was added and the reaction mixture was maintained at reflux for an additional 8 hours. The CH$_3$CN was removed by rotary evaporation. CH$_2$Cl$_2$ and 5% aq. NaHCO$_3$ were added to the residue. The mixture was stirred briefly and the resulting two layers separated. The NaHCO$_3$ layer was re-extracted twice with additional CH$_2$Cl$_2$. The organic layers were combined, dried (Na$_2$SO$_4$) and reduced. The product was purified using column chromatography [CH$_2$Cl$_2$:MeOH:pyridine (99.5:0:0.5 to 98.5:2:0.5)] (27 mg: 37%); $^1$H NMR (CDCl$_3$) δ 9.02 (d, J=2.1 Hz, 1H, H$_3$ of DNP), 8.46 (s, 1H, H$_6$), 8.07 (dd, J=9, 2.4 Hz, 1H, H$_5$ of DNP), 7.35–7.09 (m, 10H, H6 of DNP and Ar), 6.75–6.64 (m, 4H, Ar), 6.41 (dd, J=9, 2.4 Hz, 1H, H$_{1'}$), 4.70 (m, 1H, H$_{3'}$), 4.16 (m, 1H, H$_4$), 3.73 (2s, 6H, 2CH$_3$), 3.38 (d, J=7.5 Hz, 2H, H$_{5'}$), 2.64 (m, 1H, H$_{2'}$), 2.44 (m, 1H, H$_{2'}$); UV (0.1 M TEAA, pH 7.1 with 82% CH$_3$CN) 264, 324 nm; HR FAB MS calculated for C$_{36}$H$_{32}$N$_4$O$_{11}$S (M)$^+$728.1788 found 728.1802 (1.9 ppm). (Synthesized by the method of Bleasdale et al. (Bleasdale et al., 1990)).

Synthesis of 5'-O-(4,4'-dimethoxytrityl)-5-S-(2,4-dinitrophenyl) mercapto-2'-deoxyuridine-3'-O-(2-cyanoethyl-N,N'-diisopropyl) phosphoramidite (Compound 7).

Compound 6 (13 mg, 18 μmol) was dried under vacuum in the reaction vessel. Anhydrous CH$_3$CN (0.3 mL) was added and the reaction vessel was transferred to an atmosphere bag filled with dry N$_2$. A mixture of 2-cyanoethyl-N,N,N'N'-tetraisopropylphosphorodiamidite (5.5 μL, 17 μmol) and tetrazole (1.3 mg, 18 μmol) in anhydrous CH$_3$CN (50 μL) was added. The reaction mixture was maintained at room temperature for 30 min. An additional mixture of 2-cyanoethyl-N,N,N'N'-tetraisopropylphosphorodiamidite (2.3 μL, 7.2 μmol) and tetrazole (0.6 mg, 8.3 μmol) in anhydrous CH$_3$CN (25 μL) was added and the reaction mixture was stirred for 30 min. CH$_2$Cl$_2$ (20 mL) and 5% (w/v) aq. NaHCO$_3$ (15 mL) were added to the mixture; the organic layer was removed and re-extracted with water, dried (Na$_2$SO$_4$) and evaporated. The residue was subjected to column chromatographic purification [CH$_2$Cl$_2$:MeOH:pyridine(99.5:0:0.5 to 98.5:1.0:0.5)] to obtain Compound 7 (8.6 mg, 52%). The yellow product was analyzed by analytical RP HPLC using a gradient of buffer A and acetonitrile [70% (v/v) CH$_3$CN to 80% in 3 min.; 80% CH$_3$CN to 100% in 15 min.]. UV absorption was monitored at wavelengths of 254 and 330 nm. The diastereomers eluted at 11.09 and 12.49 min. UV scans of the diastereomers showed absorption peaks at 264 and 327 nm. Phosphorus NMR indicated the presence of two diastereomers [$^{31}$P NMR (CDCl$_3$) δ 149.12, 149.27 ppm].

Example 2

Automated Synthesis of an Oligonucleotide Containing 5-SDNP-dU

Synthesis and Purification of Oligonucleotides.

Oligonucleotides were synthesized on an Applied Biosystems 392 DNA Synthesizer using the standard β-cyanoethyl-protected phosphoramidite method. A series of three modified oligonucleotides were prepared on a 40 nmole scale using a Trityl On method. The thiol-protected analog, Compound 7, was manually dissolved into anhydrous acetonitrile at a concentration of 0.027 M and the solution was attached to the spare port on the DNA synthesizer. As the concentration of Compound 7 was lower than the concentration of the commercial phosphoramidites used in these syntheses (0.05 M), the coupling time for the modified analog was increased by 120 seconds. Syntheses of the corresponding unmodified oligonucleotides were also performed. The sequences of the oligonucleotides are shown in Table 1.

Figure 2:
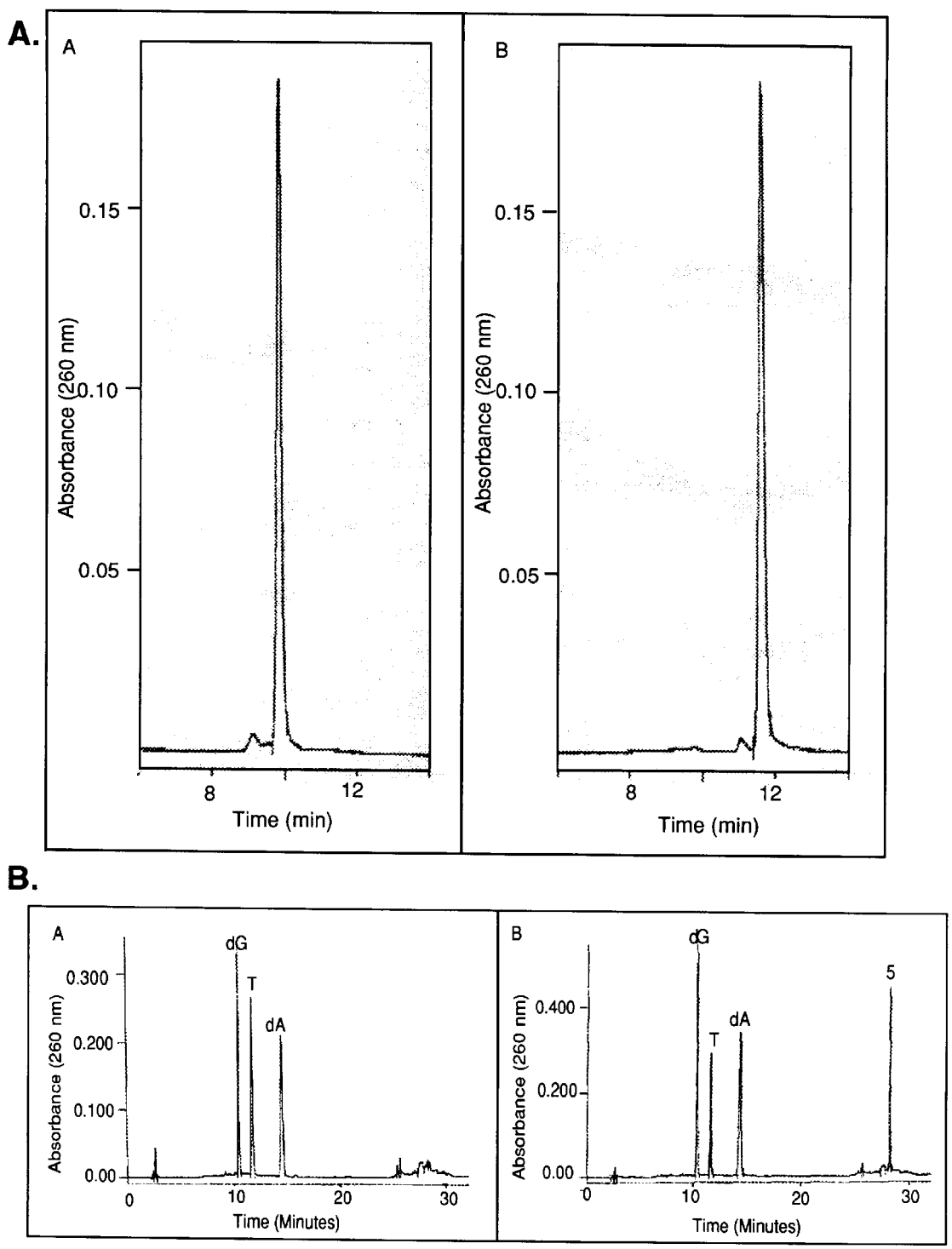
FIG. 2.
Figure 3:
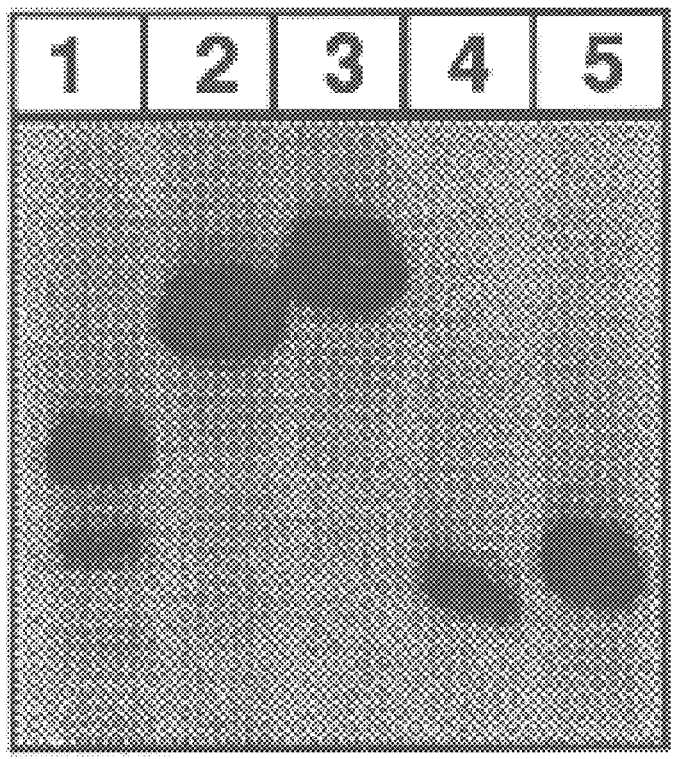
FIG. 3: A.: Gel electrophoretic analysis of DNP-labeled oligonucleotides. The [$^{32}$P] labeled oligonucleotides C-F (Table 1) were analyzed by electrophoresis on a 25% polyacrylamide-7M urea gel (acrylamide/methylene bisacrylamide=19:1). Lane 1: Commercial 24-mer marker, CGC GGA ATT CTC ATG CAT TGC CCA (SEQ ID No: 1); Lane 2; 24-mer, Oligonucleotide E; Lane 3: DNP-labeled 24-mer, Oligonucleotide F; Lane 4: 22-mer, Oligonucleotide C; Lane 5: DNP-labeled 22-mer, Oligonucleotide D. B.: Gel electrophoretic analysis of the deprotection and alkylation reactions. oligonucleotides E and F were reacted with 1.4 M BME. Half of these reactions were alkylated with 5-IAF. The treated oligonucleotides were analyzed by electrophoresis on a 25% polyacrylamide-7M urea gel (acrylamide/methylene bisacrylamide=19.1). Lane 1: Oligonucleotide E+1.4 M BME at room temperature; Lane 2: Lane 1 reaction+5-IAF; Lane 3: Oligonucleotide E+1.4 M BME at 45° C.; Lane 4: Lane 3 reaction+5-IAF; Lane 5: Oligonucleotide F+1.4 M BME at room temperature; Lane 6: Lane 5 reaction+5-IAF; Lane 7: Oligonucleotide F+1.4 M BME at 45° C.; Lane 8: Lane 7 reaction+5-IAF.
Figure 3:
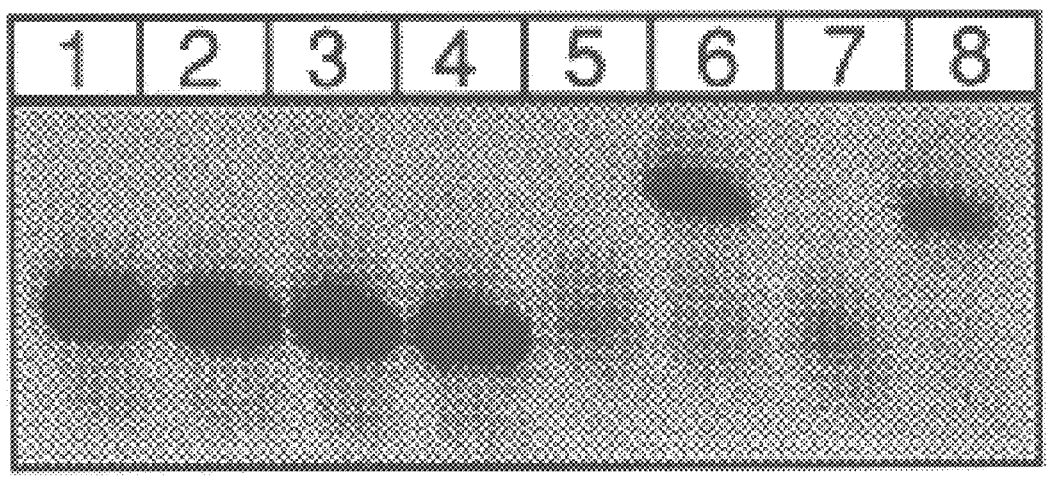

The oligonucleotides were removed from the column by treatment with concentrated $NH_4OH$ (1 mL). Deprotection of the exocyclic amines was then accomplished by treatment of the oligonucleotides with an additional 1 mL of fresh concentrated $NH_4OH$ at room temperature for 44 hours. The $NH_4OH$ solution was concentrated using a Savant Speed Vac without heat. Small portions of $Et_3N$ were periodically added to the concentrating solution to maintain a basic pH. The crude oligonucleotides were re-dissolved in 10 mM TEAB (pH 7.1) and purified as the DMT ethers using semi-preparative RP HPLC. Two different gradients of buffer B and acetonitrile were utilized. The shorter oligonucleotides (7 and 22 nucleotides) were purified with an elution gradient of $CH_3CN$ from 5% (v/v) to 30% in 15 min. then 30% to 100% in 5 min. The 24-mer oligonucleotides were purified with an elution gradient of $CH_3CN$ from 5% to 30% in 18 min. then 30% to 100% in 5 min. The appropriate fractions were evaporated to dryness using a Jouan Concentrator without heat. Following purification of the oligonucleotides, the DMT group was removed by treatment with 80% (v/v) HOAc (200 μL) at room temperature for 20 min. The oligonucleotides were ethanol precipitated and re-dissolved into 300 μL of nanopure water and stored at −20° C. The purity of the oligonucleotides was analyzed by analytical RP HPLC (FIG. 2A, oligonucleotides A and B shown). Elution of the oligonucleotides was performed using a linear gradient of $CH_3CN$ (5 to 20% in 15 min.) with buffer B. The purified oligonucleotides were also analyzed by 25% polyacrylamide-7 M urea gel (acrylamide/methylene bisacrylamide=19/1) (FIG. 3A, Oligonucleotides C–F shown).

Enzymatic Digestion with Nuclease P1 and CIP

The oligonucleotides A and B were subjected to enzymatic digestion. The pure oligonucleotides were incubated with Nuclease P1 (2 U) at 37° C. for 6 hours in a total volume of 50 μL of buffer C. Five microliters of 10× buffer D and 43 μL of $H_2O$ were added to the reaction. CIP (2 U) was added and the pH of the reaction was adjusted with 5% (v/v) NaOH (0.8 μL). The reaction mixture was incubated overnight at 37° C. To recover the nucleosides, 11 μL of 3 M NaOAC, pH 5.3 and 250 μL of absolute EtOH were added to the reaction mixture. The mixture was stored at −80° C. for 4 hours and then centrifuged at 14000 rpm for 20 min. The supernatant fraction was removed and concentrated. The resulting residue was re-dissolved into 35 μL of buffer A and analyzed by analytical RP HPLC (FIG. 2B). The elution gradient consisted of buffer A with an increasing concentration of $CH_3CN$ (0% to 5% in 5 min., 5% to 6% in 15 min., 6% to 50% in 5 min. and finally 50% to 80% in 15 min.). The UW absorption was monitored at 260 and 330 nm. Commercial nucleosides and monophosphates of dA, dC, dG and T were utilized as standards. Synthetic 5-S-(2, 4-dinitrophenyl) mercaptodeoxyuridine (Compound 5) was also utilized as a standard. An enzymatic digestion without oligonucleotide was performed to identify background peaks arising from the buffer and enzymes.

Deprotection and alkylation of a DNP-modified oligonucleotide

Oligonucleotide F (100 pmol) was radiolabeled by reaction with T4 Polynucleotide Kinase using [γ-$^{32}$P]ATP. The labeled oligonucleotide F was isolated by ethanol precipitation and re-dissolved into 30 μL $H_2O$. The oligonucleotide (4.5 μL) was treated with 1.4 M BME either at 45° C. for 4 hours or at room temperature for 12 hours in a 20 μL solution of 20 mM Tris-HCl, pH 8.2. Following this deprotection to remove the DNP group, half of the reaction mixture was precipitated with ethanol while the other half of the mixture was subjected to alkylation conditions with 5-IAF. The corresponding unmodified oligonucleotide E was treated identically to serve as a control.

To recover the deprotected oligonucleotides by ethanol precipitation, 0.36M NaOAc, pH 5.6 (100 μL), 1M $MgCl_2$ (1.2 μL) and nanopure water (10 μL) were added to the reaction mixture (10 μL) to provide a final volume of 121 μL. Absolute ethanol (300 μL) was added and the mixture was cooled at −80° C. The oligonucleotides were pelleted by centrifuging at 14000 rpm for 20 min. The supernatant was removed and the pellet was washed with cold 95% (v/v) ethanol. The mixture was chilled for 20 min. in a dry ice/ethanol bath and spun at 14000 rpm for 20 min. Following the removal of the supernatant fraction, the recovered oligonucleotides were dissolved into 20 μL of nanopure water. Mixtures of oligonucleotides (4.5 μL), 100 mM DTT (0.5 μL) and buffer E (5 μL) were prepared and analyzed by electrophoresis on a 25% polyacrylamide-7 M urea gel (acrylamide/methylene bisacrylamide=19/1) (FIG. 3B).

Alkylation of the deprotected thiol moiety was accomplished by the addition of 15 μL of 20 mM Tris-HCl (pH 4.8) to 10 μL of the deprotection reaction (pH 8.2). Following this addition, the pH of the alkylation reaction was 7 (as judged by pH paper). One microliter of 10 mM 5-IAF in DMF was added and the reaction mixture was maintained at room temperature overnight. The oligonucleotides were recovered by ethanol precipitation and re-dissolved into 20 μL nanopure water. The alkylated oligonucleotides (4.5 μL) were mixed with 100 mM DTT (0.5 μL) and buffer E (5 μL) and analyzed by electrophoresis on a 25% polyacrylamide-7M urea gel (acrylamide/methylene bisacrylamide=19/1) (FIG. 3B).

DNA Synthesis via PCR using a DNP-modified oligonucleotide

Figure 4:
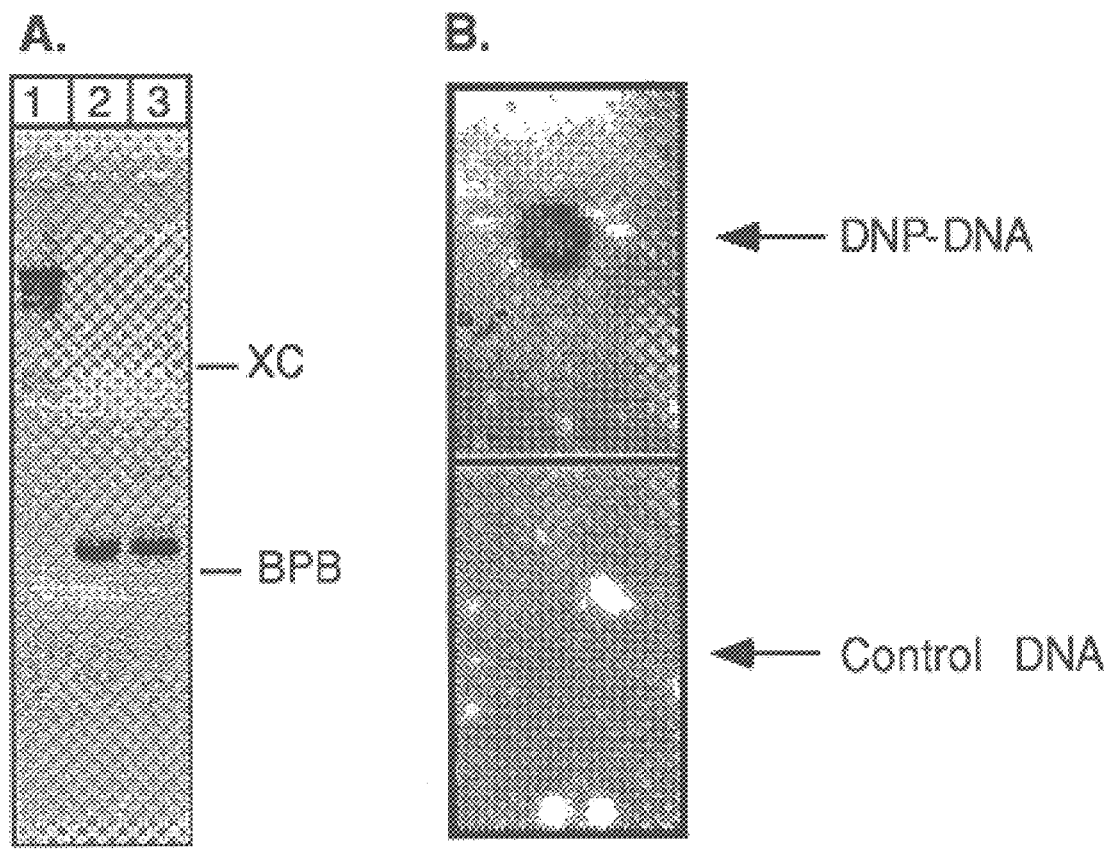
FIG. 4: Analysis of PCR products.

PCR reactions were performed on a Perkin Elmer Cetus Gene Amp PCR System 9600. The DNA fragment containing the bacteriophage lambda PR' promoter, 6S gene, and tR' terminator, with the lambda qut site (Yang et al., 1987) was amplified from plasmid pHA100 (Zhang & Hanna, 1995) using either oligonucleotide E or F and the universal T7 primer (Stratagene). The DNA product was purified by excision of the band from an agarose gel and extraction of the DNA using the commercially available GENECLEAN kit (BIO 101 Inc., La Jolla, Calif.). The PCR products were dissolved into equal volumes of buffer F and analyzed by electrophoresis on a 1.5% agarose gel. Detection of DNA was achieved by addition of ethidium bromide to the electrophoresis buffer. (FIG. 4A).

Immunodetection of DNP-labeled DNA.

Dot blot experiments were performed manually. The DNP-labeled PCR product and the corresponding unlabeled DNA fragment (1 pmole each) were in 10× SSC solution (1.5 M NaCl, 0.15 M $Na_3$Citrate, pH7). Samples (13 μL) were applied to a pre-wetted charged nylon membrane (Zeta Probe GT; Biorad). The membranes were air dried, rinsed briefly with 2× SSC and heated at 80° C. under vacuum for 30 min. The membranes were blocked by overnight incubation at 4° C. in TBS-T (20 mM Tris HCl, 500 mM NaCl, 0.4% (v/v) Tween 20, pH 7.6) containing 10% (w/v) dried milk. The membranes were then washed with TBS-T two times briefly, one time for 15 min., and two times for 5 min. The membranes were incubated with a 1:1500 dilution of anti-DNP antibodies for 1 hour, washed as described above and then incubated with a 1:10,000 dilution of horseradish peroxidase-linked whole anti-rabbit Ig for 1 hour. Membranes were then washed one time for 15 min. and 4 times for 5 min. with TBS-T. Detection of the antibodies was carried out using the ELC chemiluminescence method (Amersham). The membranes were incubated with the detection agents for 1 min. before exposure to x-ray film for 2 min. (FIG. 4B).

RESULTS

The synthesis and characterization of a novel deoxyuridine phosphoramidite (Compound 7) containing a protected thiol group at the 5 position of the mercaptopyrimidine ring is described (FIG. 1). This DNP-labeled analog was site-specifically incorporated internally into a series of oligonucleotides. Significant differences in overall synthetic yields were not observed between oligonucleotides made with normal deoxynucleoside phosphoramidites and those which contained the analog, indicating that the modified phosphoramidite is a suitable reagent for automated oligonucleotide synthesis. Enzymatic digestion of the DNP-labeled oligonucleotide established the stability of the modified pyrimidine to the conditions for chemical synthesis and purification of oligonucleotides (FIG. 2B). Selective deprotection of the 5-thiol moiety with BME and subsequent modification of the unmasked thiol with 5-IAF were verified by gel electrophoresis of the oligonucleotides (FIG. 3B). Incorporation of the DNP-labeled oligonucleotide into double-stranded DNA was achieved using PCR. Isolation and characterization of the PCR products included gel electrophoresis and immunodetection with anti-DNP antibodies (FIG. 4A and B).

Synthesis

Synthesis of the deoxyuridine phosphoramidite analog (Compound 7) was carried out following the sequence of reactions outlined in FIG. 1. Compounds 2–7 have not been previously described in the literature. The method chosen for incorporation of the thiol group required thiocyanation of the pyrimidine ring. Initially, this reaction was performed on deoxyuridine and the reaction conditions utilized were similar to those previously described (Bradley & Hanna, 1992; Nagamachi et al., 1974; Torrence et al., 1968). Although literature reports indicate yields of 54% for the thiocyanation of deoxyuridine, this was difficult to achieve. The yield for this reaction varied considerably and was at times as low as 9%. A major side product in this reaction was isolated and identified by NMR and IR as 5'-O-acetyl-5-thiocyanatodeoxyuridine indicating that along with thiocyanation, acetylation of the sugar ring had occurred.

To circumvent the problems associated with the reaction described above, 3',5'-O-diacetyl-2'-deoxyuridine (Compound 1) was utilized as the starting material. Protection of the sugar hydroxyls by acetylation prior to thiocyanation results in higher yields (95%) for the reaction (Nagamachi et al., 1974). However, removal of the acetyl protecting groups could not be accomplished using standard basic conditions required for deesterification without destruction of the thiocyanato group. Therefore, a synthetic approach was developed which required reduction of the thiocyanato compound to the mercapto analog prior to removal of the acetyl groups (FIG. 1). Thibcyanation of the 3',5'-O-diacetyl-2'-deoxyuridine (1) was achieved following the literature procedure described above except that the crude material was extracted with petroleum ether to remove nonpolar impurities prior to column chromatographic purification. The pure product was obtained in 82% yield as a white solid.

Reduction of the thiocyanato derivative 2 to the mercapto analog (Compound 3) was achieved by reaction with DTT in a solvent mixture of MeOH and 0.1 M EDTA (pH=7.8). This reaction is a variation of a reported procedure (Lin et al., 1988) for the reduction of 3'-azido-2',3'-dideoxy-5-thiocyanatouridine; this mercapto analog however was not isolated. Purification of Compound 3 was achieved by acidification of the reaction mixture followed by concentration of the mixture. The residue was extracted with $CH_2Cl_2$ and $H_2O$. The presence of the acetyl groups insured the product was organic solvent soluble. In order to remove residual DTT, the organic layer was reduced and the residue triturated with water to crystallize the product as well as to dissolve residual DTT. Compound 3 was obtained as a white solid in 75% yield.

The mechanism for the reduction of the thiocyanato requires displacement of the cyano group by DTT. Since no attempt was made to remove the cyanide ion before acidification of this reaction mixture, every step of the isolation of Compound 3 from acidification to trituration with $H_2O$ was performed in a fume hood. This synthesis of Compound 3 was designed for the preparation of both 5-alkyldithio and 5-alkylthio or 5-arylthiopyrimidine analogs. To prevent degradation of the 5-alkyldithio compounds by DTT, purification of Compound 3 was necessary. This is not the case with formation of 5-alkylthio pyrimidines (Lin et al., 1988) and this purification step has been eliminated for Compound 4 resulting in a slight decrease in yield.

The DNP protecting group has been employed in oligonucleotide synthesis as a protecting group for 6-mercaptopurine and 6-thioguanine phosphoramidites (Xu et al., 1992a; Xu et al., 1992b) and as a functional moiety on a non-nucleoside phosphoramidite (Grzybowski et al., 1993). These studies indicated the DNP group was stable during automated DNA chemical synthesis. Conversion of mercaptan 3 into the 2,4-DNP analog 4 was achieved by reaction with 2,4-dinitrofluorobenzene in anhydrous $CH_3CN$ with $Et_3N$ present as a catalyst (Xu et al., 1992b). The product was isolated as a yellow solid in 88% yield. Attachment of the thiol protecting group prior to removal of the acetyl moieties insured that the product was soluble in organic solvents, which aided in the purification of the material. More importantly, protection of the sulfur inhibits the oxidation of the analog to the disulfide compound, a potential reaction of 5-mercaptopyrimidines (Kalman & Bardos, 1967).

Another method of preparing 5-arylthiol ethers of deoxyuridine has been previously described. Bergstrom et al. has prepared a series of alkyl and aryl mercaptodeoxyuridine analogs using a palladium-mediated reaction between 5-(chloromercuri)-2'-deoxyuridine and the appropriate disulfide (Bergstrom et al., 1991). Although this method offers a simple route to arylthiol ether analogs it was not selected for study. Development of a more versatile intermediate such as Compound 3 which can be easily converted into various types of analogs including disulfides was desired for future studies. Additionally, the synthetic utility of the method has not been fully evaluated and therefore formation of the desired dinitrophenyl analog (Compound 5) was uncertain.

Deesterification of nucleosides is commonly performed under basic conditions using $NH_3$ or NaOMe (Kini et al., 1989; Trivedi & Bruns, 1989). Literature reports suggest the DNP group is marginally stable to nucleophiles such as NaOMe; the stability of this group being strongly dependent on the reaction conditions (Greene, 1981). Successful removal of the acetyl groups was achieved by reaction of the diacetyl analog (Compound 4) with NaOMe in MeOH without an apparent loss or modification of the DNP group as judged by NMR and IR. Following the deacetylation, the diol (Compound 5) was isolated as a yellow solid in 81% yield. An initial attempt to deacetylate Compound 4 under mild reductive methods was performed (Brown et al., 1982; Soai & Ookawa, 1986). However, reaction with LiBH$_4$ in a mixture of Et$_2$O and MeOH did not result in the formation of Compound 5, possibly due to the poor solubility of the starting material.

Incorporation of the DMT protecting group at the 5' position of nucleosides is typically accomplished by reaction with DMTCl in the presence of pyridine or dimethylpyridine (Chaudhary & Hernandez, 1979). However, as utilization of these conditions with other 5-thiol modified nucleosides was not successful (unpublished results), this reaction was not attempted for the synthesis of Compound 6. Conversion to the 5'-dimethoxytrityl analog (Compound 6) was achieved by reaction of Compound 5 with DMT$^+$BF$_4$— in the presence of DBMP in CH$_3$CN at reflux. This reagent, DMT$^+$BF$^-_4$, has only recently been utilized in the preparation of 5' protected nucleosides (Bleasdale et al., 1990; Lakshman et al., 1992).

The proposed mechanism for dimethoxytritylation with DMTCl and pyridine requires formation of a dimethoxytrityl pyridinium salt which then undergoes reaction with the 5' hydroxyl group (Chaudhary & Hernandez, 1979). Formation of the pyridinium salt is considered the limiting step. The reagent DMT$^+$BF$^-_4$ serves as a source for the dimethoxytrityl cation. By preforming the cation prior to reaction, the slow step in the dimethoxytritylation has been eliminated and the ether should be more easily formed. Although Compound 6 was obtained using this reagent, the reaction was performed under reflux conditions. It is unclear why the reaction requires such stringent conditions but presumably steric hindrance plays some part. Modification of other bases has been reported to inhibit dimethoxytritylation possibly due to steric hindrance (Cosstick & Douglas, 1991).

Silica gel column chromatography was employed to isolate Compound 6. Due to the acidic nature of the silica gel, a small percentage of pyridine was added to the eluting solvent to prevent loss of the acid sensitive DMT group. Initially, Et$_3$N was used in the solvent system; however triethylammonium salts of Compound 6 were isolated as determined by NMR. This was not observed during the synthesis of the standard 5'-dimethoxytrityl-2'-deoxyuridine. Switching to pyridine, a weaker base, in the eluting solvent system eliminated this problem. A satisfactory high resolution FAB mass spectra was obtained for Compound 6.

The Compound 6 was isolated as a yellow solid in yields ranging from 35 to 48%, making formation of the dimethoxytrityl ether the lowest yielding reaction in this synthetic sequence. However, approximately 20% of the starting material, Compound 5, was converted into the 3',5'-bis (dimethoxytrityl) analog, which was isolated and converted back into 4 for recycling into the synthesis.

The final reaction in the preparation of Compound 7 is the incorporation of the phosphoramidite moiety at the 3' position of the nucleoside. This is commonly accomplished by reaction of the appropriately protected nucleoside with 2-cyanoethyl-N,N-diisopropyl chlorophosphoramidite in the presence of the N,N-diisopropylethylamine (DIEPA) (Sinha et al., 1984). Utilization of these conditions did not result in the desired product and starting material was re-isolated. However, a standard reaction with 5'-dimethoxytrityldeoxyuridine was successful. A second method for incorporation of the phosphoramidite moiety which utilizes the reagent 2-cyanoethyl-N,N,'N'-tetraisopropylphosphorodiamidite in the presence of tetrazole in CH$_3$CN was evaluated (Barone et al., 1984). Unlike the basic reaction with DIEPA, these slightly acidic conditions provided the DNP-labeled phosphoramidite, Compound 7. RP HPLC analysis of Compound 7 indicated the presence of a pair of closely eluting peaks (11.0 and 12.4 min) representative of the expected 1:1 mixture of diastereomers. The overall purity of the sample was determined to be greater than 96% and no starting material was observed in the chromatogram. HPLC data was quantified using a simple area percent method. Similar results were observed using silica gel TLC analysis (CH$_2$Cl$_2$:MeOH:Et$_3$N;96:3:1). The phosphorous NMR spectrum showed two characteristic peaks associated with the diastereomeric phosphoramidites (149.12 and 149.27 ppm). An additional peak appeared in the NMR at 14.3 ppm. Based on the chemical shift of this peak, the impurity is presumed to be a hydrolysis product (Scremin et al., 1994). No attempt was made to remove this material prior to oligonucleotide synthesis as it is not reactive in the oligonucleotide chemistry. A high resolution FAB mass spectrum could not be obtained for Compound 7 due to its instability during analysis. This was not surprising as the standard deoxyuridine phosphoramidite displayed a high degree of instability during high resolution FAB MS analysis; however, a small molecular ion peak was identified in the spectrum. Evaluation of Compound 7 using low resolution mass spectroscopy showed a fragment (m/z=407) consistent with the loss of the DMT and the phosphoramidite moieties. As a similar fragmentation pattern was observed for the standard deoxyuridine phosphoramidite under these experimental conditions, the information supports the proposed structure.

Syntheses and purification of oligonucleotides

Internal incorporation of the phosphoramidite analog, Compound 7, into series of oligonucleotides has been accomplished using an automated DNA synthesizer. The natural oligonucleotides with corresponding sequences were prepared as standards. The sequences for the oligonucleotides which are listed in Table 1 were chosen for two reasons: the 7-mer was designed for characterization purposes while the 22-mer and the 24-mer were developed to study the DNA-protein interactions during transcription of the bacteriophage lambda 6S gene. The concentration of the phosphoramidite solution of Compound 7 was diluted twofold as compared to the normal phosphoramidites (dA, dG, T and dC) utilized in these DNA syntheses. This dilution was performed to conserve material. The coupling time for the reaction involving the modified phosphoramidite was increased by 120 seconds. Under these reaction conditions, the coupling yield for the modified phosphoramidite was >96% which was comparable to the coupling yields of the other standard phosphoramidites. The average stepwise yields for all six oligonucleotide syntheses were determined automatically by the ABI synthesizer using a trityl cation assay. These yields are listed in Table 1.

TABLE 1

SEQUENCE AND CHARACTERIZATION DATA
FOR THE SYNTHETIC OLIGONUCLEOTIDES

| No. | Sequence[a] | ASWY (%)[b] | Overall Yield (%)[c] | RT (min)[d] |
|---|---|---|---|---|
| A | gta tgt a | 97.5 | 62.1 | 9.8 |
| B | gta ngt a | 98.1 | 50.1 | 11.6 |
| C | gac tca acg atg ggt taa ttc g (SEQ ID NO:3) | 98.0 | 40.2 | 9.6 |
| D | gac tca acg ang ggt taa ttc g (SEQ ID NO:4) | 97.9 | 41.0 | 10.0 |
| E | ggg taa att tga ctc aac gat ggg (SEQ ID NO:5) | 97.6 | 21.9 | 9.7 |
| F | ggg naa att tga ctc aac gat ggg (SEQ ID NO:6) | 97.2 | 28.1 | 10.5 |

[a]n denotes the position of the thiol modified nucleoside;
[b]ASWY = average stepwise yield for nucleotide addition;
[c]Overall yield = O.D. of purified oligonucleotide/O.D. of crude oligonucleotide × 100%;
[d]Retention time of purified oligonucleotide during RP HPLC analysis Selective removal of the exocyclic amine protecting groups in the presence of the DNP moiety was achieved by treatment with $NH_4OH$ at room temperature for 44 hours. Typically, this deprotection is performed at elevated temperatures of 55° C. for 8 hours (ABI technical bulletin #13, 1987). However, studies involving reaction of the DNP-labeled nucleoside 5 with conc $NH_4OH$ at 55° C. indicated the analog was not stable to these conditions but was stable at room temperature (data not shown). As successful removal of standard exocyclic amine protecting groups at room temperature has been reported for other oligonucleotides containing modified phosphoramidites, these conditions were utilized (Sheardy & Seeman, 1986). Although these initial studies were performed with the standard exocyclic amine protecting groups, phosphoramidites containing a wide variety of protecting groups which can be efficiently removed under mild conditions are now commercially available. These will be investigated for compatibility with phosphoramidite Compound 7.

The crude oligonucleotides were purified as the DMT ethers by RP HPLC. Removal of the DMT group under standard acidic conditions did not affect the DNP moiety. Following removal of the DXT group, the oligonucleotides were analyzed for purity by both analytical RP HPLC and gel electrophoresis as shown in FIGS. 2A and 3A respectively. The oligonucleotides showed one major product in both analyses. The retention times of the DNP-labeled oligonucleotides were greater than the corresponding natural oligonucleotides in the HPLC analyses due to the lipophilic nature of the dinitrophenyl group. The RP HPLC retention times for the purified oligonucleotides are listed in Table 1. The overall yields of the pure material which were calculated by dividing the optical density of pure oligonucleotide by the optical density of crude DMT-labeled oligonucleotides times 100% are found in Table 1 (Kuimelis & Nambiar, 1994). The yields for the corresponding normal and DNP-labeled oligonucleotides were comparable.

Enzymatic digestion of the heptanucleotide

To establish that the DNP group is stable to the conditions of automated DNA synthesis, deprotection, and purification, a DNP-labeled oligonucleotide was enzymatically digested into its corresponding nucleosides and evaluated by RP HPLC. In order to observe the single DNP-labeled nucleoside present in the enzymatic digest, the short chain oligonucleotide B was used for this analysis. The sequence chosen for this heptanucleotide did not contain deoxycytidine. Deoxycytidine co-elutes with 5-mercaptodeoxyuridine, a potential side product arising from the loss of the DNP group, in the gradient system utilized in the analysis. Deoxycytidine was therefore omitted from the sequence to eliminate uncertainty in identifying the nucleoside peaks. 5-Mercaptodeoxyuridine was synthetically prepared in this lab by reduction of 5-thiocyanatodeoxyuridine (Nagamachi et al., 1974).

Initial degradation of the oligonucleotide B and the corresponding normal oligonucleotide A was attempted by concurrent digestion with snake venom phosphodiesterase (SVP) and CIP (Kuimelis & Nambiar, 1994). This method proved useful in the digestion of the natural oligonucleotide but did not appear to fully degrade the DNP-labeled material. This is consistent with other studies in which SVP has failed to function with some modified oligonucleotides and nucleotides (Gao et al., 1992; Hanna et al, 1989; Hanna et al., 1993). Substitution of the exonuclease SVP with an endonuclease Nuclease P1 resulted in complete digestion. Due to a difference in the pH requirements of these enzymes for activity, this digestion was accomplished in two consecutive enzymatic reactions. First, Nuclease P1 cleaved the phosphodiester bonds to provide the 5'-monophosphates which were then subjected to treatment with CIP. The resulting nucleosides were isolated and analyzed by RP HPLC. The results are shown in FIG. 2B.

This enzymatic degradation provided the correct ratios of unmodified and modified nucleotides. For oligonucleotide A, the ratio of dA, dG and T was 1.9:2.1:2.9. For oligonucleotide B, the nucleoside 5 is also expected in the reaction mixture providing a ratio of dA, dG, T and 5 of 1.9:2.1:1.9:1.1. Chemically synthesized Compound 5 was utilized as a standard. Both the enzymatically obtained and the chemically obtained nucleoside Compound 5 eluted with the same retention time during RP HPLC analysis. In addition, these compounds provided identical UV spectra with absorption peaks appearing at 262 and 334 nm. Finally, no unidentifiable peaks were observed in the HPLC chromatograms of the enzymatic digests and only one peak representing nucleoside Compound 5 appeared in the HPLC chromatogram monitored at 330 nm. In this analysis, absorption at 330 nm is associated with the presence of either the dinitrophenylthiol ether or the 5-mercaptopyrimidine moiety. If the DNP-labeled analog had undergone modification during automated DNA synthesis, deprotection, or purification, extraneous peaks were predicted to appear in this chromatogram.

Deprotection and alkylation of a DNP-modified oligonucleotide

Removal of the DNP moiety was accomplished by reaction of oligonucleotide F with 1.4 M BME in Tris buffer pH 8 (Shaltiel, 1967). The reaction was performed under two different reaction conditions: room temperature for 12 hours and 45° C. for 4 hours. Oligonucleotide E was reacted under the same conditions to serve as a standard. No attempt was made to isolate the deprotected oligonucleotide prior to modification with 5-IAF. The pKa of BME is 9.6 while the pKa of 5-mercaptodeoxyuridine is 5.0 (Bardos & Kalman, 1966). Modification of a thiol by reaction with haloacetamido compounds such as 5-IAF requires formation of the thiolate anion. By lowering the pH of the reaction mixture, the selectivity for modification of the oligonucleotide is enhanced over that of BME, a potential side reaction. The oligonucleotide products in both the deprotection and modification reactions were isolated by ethanol precipitation and analyzed by electrophoresis using a 25% polyacrylamide-7 M urea gel. The results are shown in FIG. 3B. Lanes 1 through 4 represent reactions utilizing oligonucleotide E. No difference is observed in these four lanes indicating the natural oligonucleotide structure is stable to the conditions needed for deprotection and alkylation of the thiol. Lanes 5 and 7 represent reactions of oligonucleotide F with BME at room temperature and 45° C. respectively, while lanes 6 and 8 depict the corresponding alkylation reactions which were carried out at room temperature. No apparent mobility shift is observed between the natural oligonucleotide (lanes 1–4) and lanes 5 and 7, which is consistent with our observations that a 20-mer RNA containing 5-SH-UTP co-migrates in this gel system with 20-mer containing no analog (He et al., 1995). In contrast, a substantial difference is observed following modification with fluorescein, consistent with other reports of gel mobility shifts of fluorescein-labeled oligonucleotides (Clegg et al., 1992; Mergny et al., 1994). In fact, the selection of 5-IAF for the alkylation experiments instead of a thiol-modifying photocrosslinking reagent such as p-azidophenacyl bromide (APB) was due in part to the ease in which the reaction results could be monitored by gel electrophoresis. The conditions for alkylation of the oligonucleotide with. 5-IAF however should prove useful with other haloacetyl derivatives such as APB. We have specifically labeled the thiol group in an RNA molecule containing 5-SH-UMP (He et al., 1995) with APB. We have also attached APB to a DNA molecule generated by PCR with a oligonucleotide containing (compound 7), after BME removal of the DNP group (not shown).

As the mobility shift associated with the DNP label is small (FIG. 3A), it is possible that a mixture of DNP-labeled and 5-mercapto-labeled oligonucleotides may appear as one band on a 25% polyacrylamide-7 M urea gel. Therefore, one can not determine the extend to which deprotection has occurred. However, the appearance of a new band in lanes 6 and 8 (FIG. 3B) with the subsequent disappearance of the band seen in lanes 5 and 7 indicates that the oligonucleotide underwent deprotection and alkylation. Although deprotection does occur with time at room temperature, the reduced time required to deprotect at 45° C. makes this the preferred method.

PCR reaction using a DNP-modified oligonucleotide

The DNP-labeled oligonucleotide was incorporated into double stranded DNA using PCR. Plasmid pHA100 served as the template for this reaction. A 492 base pair segment of this plasmid was amplified using the universal T7 primer and either oligonucleotide E or F. The products isolated from the reaction were analyzed on a 10% polyacrylamide-7 M urea gel (data not shown) and a 1.5% agarose gel (FIG. 4A). Differences in mobility were not observed between the standard PCR product and the DNP-labeled PCR product in these gel analyses and no difference in yield was observed.

Immunodetection of DNP-labeled oligonucleotides and DNA

To insure the stability of the DNP protecting group during the PCR reaction, the products described above were subjected to immunodetection studies using rabbit polyclonal anti-DNP antibodies. The natural PCR product served as a negative control. The DNP group was detected using a chemiluminescence method and only the DNP-labeled nucleic acid provided a signal (FIG. 4B).

Example 3

Analysis of Protein-DNA Interactions Utilizing 5-S-DNP-dU

Photochemical crosslinking is a powerful technique for characterization of both RNA-protein and DNA-protein interactions in nucleoprotein complexes. Photochemical crosslinking "traps" weak or transient associations which might not survive isolation procedures such as immunoprecipitation, gel filtration, or filter binding. There are a number of approaches which can be taken in photochemical crosslinking. One involves direct irradiation of a nucleoprotein complex with short wavelength ultraviolet light. This method relies upon the direct excitation of nucleotides or amino acids to generate chemically reactive species. Such nonspecific labeling can reveal whether a protein-nucleic acid interaction exists, but there are several problems associated with this approach. These include low crosslinking yields, the inability to incorporate a crosslinking group at a specific site in the nucleic acid, and degradation of some proteins during irradiation. A second approach involves the use of nucleotide analogs modified with photoreactive crosslinking groups (reviewed in M. Hanna, 1989, Methods in Enzymology). These groups are chemically inert in the absence of light but are converted to chemically reactive species upon irradiation. Often this can be achieved with long wavelength ultraviolet or visible light, resulting in less nicking of protein or nucleic acid. Molecular contacts can be identified at the level of specific nucleotides in nucleic acids and amino acids in proteins. One can therefore gain structural information about macromolecular complexes which cannot be obtained by most other biochemical approaches.

For such mechanistic studies a variety of nucleotide analogs have been developed and utilized (M. Hanna 1989, Methods in Enzymology; Bradley and Hanna, 1992). These analogs are either tagged with a photoreactive crosslinking group or contain functional groups that can be tagged with crosslinkers after incorporation into DNA or RNA. These analogs can be incorporated into nucleic acids, either enzymatically or chemically, to analyze molecular interactions in protein-nucleic acid complexes. Upon photoactivation, analog-tagged nuecleic acids become covalently attached to adjacent macromolecules (protein, DNA, RNA) with which they have direct interactions. Therefore, nucleic acid binding domains in complexes can be characterized, nucleic acid binding proteins in extracts can be identified, and determinants involved in these specific interactions can be characterized at the level of individual nucleotides and amino acids. This methodology allows mechanistic questions about the way that specific protein-DNA or protein-RNA interactions regulate gene expression to be asked. Herein described are the approaches used to characterize the protein-DNA interactions in the E. coli transcription complex which forms on the bacteriophage lambda $P_R$, promoter.

Preparation of Site-Specifically Modified DNA Oligonucleotides

The method described here is used to probe for interactions between a specific nucleotide in DNA and a DNA-binding protein. In this case, interactions between a specific nucleotide on the non-template strand of the $P_R$, promoter are sought. The chemical approach to preparation of site-specifically modified DNA involves incorporation of a modified nucleotide during the automated synthesis of an oligonucleotide. Because the conditions used in automated oligonucleotide synthesis are rather harsh, the direct incorporation of a photocrosslinking azide group by this method is not possible, and a means for the post-synthetic incorporation of the azide group is required. 5-S-DNP-dU was incorporated into a DNA oligonucleotide, as described herein. For analysis of protein interactions with the -12 position in the nontemplate strand of the $P_R$, promoter, an oligonucleotide with the sequence 5'-5D-DNP-dU-AA ATT TGA CTC AAC GAT GGG (SEQ ID No: 2) was synthesized on an Applied Biosystems 392 DNA Synthesizer using the standard β-cyanoethyl-protected phosphoramidite method by attaching the analog to the fifth substrate port. After synthesis, removal of the oligonucleotide from the column, and removal of the exocyclic amine protecting groups, the oligonucleotide was ethanol precipitated, dissolved in water and stored at −20° C.

Analysis of 5-S-DNP-dU Effects on Hybridization Properties of ODNs

To evaluate the effect of incorporation of one or more 5-SDNP-dU analogs into oligodeoxynucleotides (ODNs) on their hybridization properties, the ODNs shown in Table 2 were synthesized. The observed melting temperatures ($T_m$) showed that incorporation of one DNP analog decreased the melting temperature by only 1.8° C. (hybrid V), compared to the normal DNA hybrid (I), and substitution with two DNP analogs caused a decrease of only 4.4° C. (hybrid VI). Therefore, the effect of a single substitution is less than that caused by a single mismatch involving unmodified nucleotides (hybrids II, III and IV vs I), and the effect of two modified analogs is still less than that of a single T-C mismatch (hybrid IV). Mismatches of 2 or more are commonly used for site-directed mutagenesis, which involves hybridization of the oligonucleotides to single-stranded DNA. Substitution with the DNP analog should therefore work as well, if not better. The use of ODNs containing one or more 5-SDNP-dU analog in assays requiring specific hybridization to a complementary strand is therefore quite feasible.

By comparison, oligodeoxynucleotides (30-mers) containing a previously described nucleobase fluorescent derivative, 5-Amido-(Carboxyfluorescein)-2'-deoxyuridine, caused decreases in melting temperature of 2° C. for ODNs with one nucleobase substitution, 6° C. for ODNs with two nucleobase substitutions, and 12° C. for ODNs containing three nucleobase substitutions (Jadhav et al. 1997). A more serious effect on the hybridization properties was observed for another previously described analog, 2-thiodeoxyuracil. Placement of even a single 2-thiodeoxyuracil analog into oligodeoxynucleotides (14-mers) caused a decrease in $T_m$ of 3–4° C. (Kuimelis and Nambiar, 1994).

TABLE 2

$T_m$ values for native and modified ODNs
ODN 1 5' GAC VCA ACG AWG GGX TAA TYC G 3'
ODN 2 3' CTG AGT TAC TZC CCA ATT AAG C 5'

| ODN Hybrid | 1 V | 1 W | 1 X | 1 Y | 2 Z | $T_m$ (° C.) | Drop in $T_m$[a] |
|---|---|---|---|---|---|---|---|
| I | T | T | T | T | A | 67.3 | 0 |
| II | T | T | T | T | G | 64.5 | 2.6 |
| III | T | T | T | T | T | 63.6 | 3.5 |
| IV | T | T | T | T | C | 61.5 | 5.6 |
| V | T | 5[b] | T | T | A | 65.5 | 1.8 |
| VI | T | 5 | 5 | T | A | 62.9 | 4.4 |
| VII | T | 5 | T | 5 | A | 62.5 | 4.8 |
| VIII | 5 | 5 | T | 5 | A | 58.0 | 9.3 |

[a] as compared to unmodified duplex (Hybrid I)
[b] 5 refers to 5-S-DNP-dU

Attachment of a Crosslinking Group at a Specific Position in DNA

The analog-modified oligonucleotide (100 pmol) was radiolabeled with T4 polynucleotide kinase using [γ$^{32}$P] ATP (FIG. 5, Step 1), isolated by ethanol precipitation and re-dissolved in water. The presence of the 5-S-DNP group on the 5' terminal nucleotide did not interfere with recognition and modification of the 5' OH group by kinase. The oligonucleotide was then incorporated into double-stranded DNA by either PCR (not shown) or by primer-extension. For primer-extension using a single-stranded phagemid DNA template, the oligonucleotide (20 pmoles) was annealed to the template (1 pmol) by heating the mixture to 75° C., cooling to 65° C. and then placing the mixture on ice (Step 2). The oligonucleotide was then extended with a thermo-stable DNA polymerase (AmpliTaq, Perkin-Elmer) by incubating for 5 minutes at room temperature and then two hours at 70° C. The template was ligated with T4 DNA ligase for 1 hour at 37° C., and then ligated DNA was isolated by ethanol precipitation (Step 3). Before addition of a crosslinking group, the DNA protecting group must be removed (Step 4). This was accomplished by treatment of the oligonucleotide (4.5 μL) with 1.4 M β-mercaptoethanol either at 45° C. for 4 hours or at room temperature for 12 hours in 20 μL 20 mM Tris-HCl, pH 8.2. The deprotected DNA was purified to remove the β-mercaptoethanol by ethanol precipitation, and the DNA was dissolved in 20 μL water. A photocrosslinking group was added to the DNA by reaction with the alkylating agent azidophenacyl bromide, and the DNA was again purified for transcription and crosslinking (Step 5).

Photocrosslinking

For UV crosslinking, the reactions are split in half; a control aliquot is kept in the dark at room temperature while the other aliquot is irradiated at room temperature for 2 minutes in a polystyrene tube 1.5 cm from a 302 nm light source (Spectroline model XX-15B, 1800 μW/cm$^2$ at 15 cm). After irradiation, DTT (to 60 mM) is added to all samples, and they are left in the dark for at least 5 minutes. After irradiation, but before protein gel electrophoresis, aliquots from the irradiated chase reactions are treated with nuclease to digest the DNA to a small radioactive fragment (Step 6). The nuclease treatment results in digestion of the DNA to small radioactive fragments. This leaves a small radioactive piece of DNA on proteins which have been crosslinked to the DNA during irradiation. The control and irradiated samples are then analyzed by gel electrophoresis and autoradiography.

Electrophoretic Analysis of Crosslinked Proteins

For identification of crosslinked proteins, samples are mixed with an equal volume of 60 mM TrisCl (pH 8.0), 60 mM DTT, 3.4% (w/v) SDS, 17% (v/v) glycerol, 0.02% (w/v) bromophenol blue, 0.02% (w/v) xylene cyanol, heated for 3 minutes at 94° C., and then analyzed on 12 cm×0.75 cm 10% SDS/polyacrylamide gels with a 4% stacking gel (acrylamide/methylene bisacrylamide=27/1). Proteins are electrophoretically blotted onto MSI NitroBind Nitrocellulose membrane (Westboro, Mass.) in 25 mM Tris, 192 mM glycine, 20% (v/v) methanol (FIG. 6A). The membrane is then silver-stained in 2% (w/v) sodium citrate, 0.8% (w/v) ferrous sulfate, 0.1% (w/v) silver nitrate for 5 minutes and dried. Autoradiography of the membranes is at −80° C. with Amersham Hyperfilm-MP and a Cronex Lightning Plus intensifying screen.

5-S-DNP-dU can be used for site-specific modification of DNA at internal and terminal positions with DNA, and molecular probes can be placed at variable distances from the DNA backbone. In addition, the commercial availability of antibodies to the DNP group allows the direct use of the DNP-labeled oligonucleotides as immunodetection probes.[15]

Example 4

Utility: Assays for Diagnosis of Bladder Cancer

Bladder Cancer strikes over 50,000 Americans every year, killing more than 11,000 (23). Currently used means to diagnose bladder cancer usually rely on immunocytochemistry, nuclear DNA content and cytology. Extensive use of highly trained labor that these tests consume make them fairly expensive to administer. In addition, while being fairly specific for the diagnosis of bladder cancer, these tests lack sensitivity. Furthermore, they are poor prognosticators of cancer progression. Tests or biopsies with better sensitivity and prognostic value are invasive, even more expensive and poorly tolerated by patients. These facts result in many patients being under-diagnosed or under-treated for their illnesses.

An ideal test would be sensitive, specific and prognostic for bladder cancer, less invasive, require fewer highly skilled scientists to administer, better tolerated by patients and less costly. Such an assay would be expected to decrease mortality and morbidity due to this disease. Such a test would also be expected to represent a significant commercial possibility since it would not only replace many of the existing tests in the marketplace but would enable an increase in the number of tests performed.

One of the methods currently used for detection of mRNA levels in a cell utilizes an RNase protection assay (Hershey and krause, 1989) which is commercially available. In an RNase protection assay, a labeled RNA probe of discrete length is constructed that includes two domains (FIG. 6). One domain compliments, and therefore hybridizes to, an mRNA species whose abundance one wishes to detect and quantify. This domain forms a double stranded RNA molecule with the intended mRNA target. The other domain is made up of sequence that does not hybridize to the intended target. In an RNase protection assay, total cell RNA (or total cellular mRNA) is incubated with an excess of an RNA probe under conditions that favor specific hybridization of the probe with the mRNA species to be detected and quantified. After the hybridization step, the RNA is digested with a mixture of RNases. All single stranded RNA is hydrolyzed down to nucleotides or short oligonucleotides. Only double stranded RNA is protected from this digestion. All of the unhybridized probe is degraded. This includes the domains of the hybridizing probes that do not complement their targets.

The digested RNAs are separated according to size by gel electrophoresis and then visualized by autoradiography. A positive signal is a labeled RNA molecule that is the correct length to be that portion of the probe that had hybridized to the intended target. This shortened form of the original probe can not be created by other means. This is why false positives are not a technical concern. Also, with an excess of probe and under the appropriate hybridization conditions, nearly all of the intended target is hybridized to the nucleic acid probe (NAP). This makes the intensity of the signal proportional to the original concentration of the target mRNA species.

The advantages of an RNase protection assay are that it is quantitative, reproducible and completely free of false positives derived from technical difficulties. This last feature makes such an assay format appealing as a technological platform for diagnostic determinations of patient derived materials. The disadvantages of an RNase protection assay are that the probes are very tedious to make. They possess very short half lives because of the radioactive isotopes ($^{32}P$) used to produce the signal. In addition, RNA is inherently less stable than DNA, and some RNases can be extremely difficult to inactivate.

The disadvantages of RNase protection are overcome by the envisioned NAP Nuclease Protection Assays (NAP-protection assays) employing the derivatizable nucleotide analogs herein. The NAPs can be synthesized in large quantities, carefully evaluated (quality control assays), and then stored for future use. There is an economy of scale that this affords which overcomes the difficulty of probe construction and synthesis. These NAPs will utilize non-isotopic means of detection, permitting the NAPs to have extended shelf lives. Additionally, the NAPs for different target mRNAs can be modified with different reporter groups. This will permit the examination of the expression of several genes simultaneously. This assay can be modified to accept automation to reduce run times.

Use of oligonucleotides or NAP probes which contain modified nucleotide analogs has been previously reported (21–23, 26–29). The chemical approach to preparation of site-specifically modified DNA involves incorporation of a modified nucleotide during the automated synthesis of an oligonucleotide. The modified oligonucleotide can then be incorporated into double-stranded DNA by PCR amplification or primer extension of a single-stranded DNA. The use of various modified phosphoramidites as masked synthons for preparing derivatized oligonucleotides at both terminal and internal sites has been reported (Xu, Zheng and Swann, 1992; Maurizi and Ginsburg, 1986). These masked synthons allow incorporation of protected functional groups such as amines (Nagamachi, et al. 1974), carboxylic acids, thiols (Goodwin and Glick, 1993) and thiocarbonyls. Once incorporated the analogs are deprotected and modified post-synthetically. Convertible nucleoside phosphoramidites, mononomers containing leaving groups, have also been used to incorporate crosslinking and photocrosslinking groups by post-synthetic substitution of the leaving group. Several companies sell reagents for the addition of molecular tags to either of the two ends of a nucleic acid (5' or 3'). Some provide reagents which allow the incorporation of more than one analog at internal positions in the NAP, to allow an increase in the amount of signal produced by the NAP, there is a resultant perturbation of nucleic acid structure or decrease in hybridization function (interaction with mRNA) of the NAP. Since the assay is based on specific NAP hybridization, with the current methods available, increasing the signal in a NAP must be balanced against the loss of hybridization capacity. However, the goal is always to obtain the strongest signal possible, because this not only decreases data acquisition time, but increases the level of sensitivity of a given assay. This is clearly an important methodology, for which a commercial market already exists.

Preferred versions of the nucleotide analogs contemplated herein have the following characteristics which make them preferable to other currently available nucleotide analogs for this assay:

1. The nucleotide modification is on a position of the base which is not required for normal RNA and DNA basepairing, therefore specific hybridization is still possible.
2. The reactive group added to the nucleotide is not normally found in DNA or mRNA (S group), therefore reaction of the probe modified oligonucleotides or NAPs with thiol-reactive alkylating agents gives virtually thiol-specific modification of the NAP. Analogs with reactive amino groups, which are modified by alkylating agents targeting amines, are less specifically modified. This is due to the presence of exocyclic amine groups in the normal nucleotides of both DNA and RNA, and these can be modified by the alkylating reagents as well.
3. The reactivity of the aryl thiol group on 5-SH-UTP to alkylating agents is considerably higher than that of alkyl thio ether derivatives ($pK_A$=5.5 vs 8,).

4. The linker attached to the nucleotide base contains all single-bonds (vs alkyl or alkynyl), thereby allowing free rotation of the probe in the region close to the nucleic acid backbone. This is advantageous because the flexibility of the linker are allows the nucleotide analogs to adopt to different enzyme active sites (in DNA and RNA polymerases), making them generally good substrates for enzymatic incorporation into nucleic acids.

5. As assessed by several functional assays, analogs modified through the aryl thio group of 5-S-U derivatives do not disturb normal RNA secondary or tertiary structures.

Unlike other types of cancer, the primary tumor in bladder cancer sheds or exfoliates relatively large numbers of cells into the lumen of the bladder. These cells can be easily collected in urine or from bladder washes. In a void urine from a patient with a bladder tumor, there will be very few to about a million cancer cells. Bladder washes yield more cells than void urines. Currently, the company UroCor, Inc. and other firms provide services to diagnose disease. Bladder cancer cells collected in urine are examined for morphology, DNA content and for protein biomarkers as detected immunochemically. While these tests are not as informative as desired, it is clear that cancer cells can be collected from patient urines and that these cells are relatively intact with respect to morphology, nucleic acid and protein content, and expression. RNA has not been directly examined in these cells, but it is reasonable to expect that the RNA content of these cells will also be intact relative to the needs of the envisioned NAP-protection assay.

A NAP-protection assay can be designed to determine the relative abundance of mRNAs for four surrogate biomarkers of bladder cancer and/or its progression relative to the abundance of a mRNA encoding a "house keeping" gene that is not differentially regulated. Changes in the abundance of the surrogate biomarkers relative to the undifferentially expressed gene will be informative in both diagnosing and evaluating the state of a patient's bladder cancer. In one embodiment, the final assay uses five probes, each specific for a different gene. One of the probes will hybridize to an appropriate "house keeping" gene. The hybridization signal from this probe will act as one of the positive controls in the assay. Of the remaining four mRNA species, targets will be selected such that in cancerous cells two of the mRNAs are increased in abundance and two are decreased relative to nontransformed cells. In this format, each regulatory pathway acts as an internal control for the other.

The following assays can be carried out to probe for mRNA levels of the human autocrine motility factor receptor, which is differentially expressed in bladder cancer cells. The DNA sequence for this gene is shown in FIG. 7.

Ribonuclease NAP Protection Assay

One ribonuclease assay is based upon the currently utilized radioisotopic RNase protection assay, described above. However, the radioactively labeled nucleotide substrates are replaced by 5-S-R-XTP nucleotides, where X is U, dU, C, or dC and R is one of several different reporter groups. The NAPs for the assay are ssRNA, which are synthesized enzymatically utilizing a bacterial or phage RNA polymerase.

In this assay, RNA NAPs can be prepared in which the RNA is labeled with many fluorescent, colormetric, chemiluminescent, or antigenic reporter groups. One such antigenic reporter group is the dinitrophenyl group (DNP), and the analog for these experiments is proposed below. The assay is the same as the current method previously described, but the protected RNA products are detected by either monitoring fluorescent emission, probing with antibodies, or monitoring chemiluminescence. In this assay, final detection still requires the analysis of the NAP protection assay by gel electrophoretic separation of the products. However, the probes can be synthesized in large quantities and stored, so this assay still has a major advantage over the existing methodologies.

Deoxyribonuclease NAP Protection Assay

An alternative nuclease protection assay can utilize DNA NAPs, similarly modified with multiple reporter groups. One compelling reason to consider DNA NAPs is that they are both chemically and biologically more stable than the comparable RNA NAPs. This makes them better prospects for synthesis in large quantities and for long storage. Despite this inherent stability relative to RNA, ssDNA can be easily degraded by single-strand specific DNases, in the manner as utilized for ssRNA digestion. In addition, with DNA NAPs, one can synthesize large quantities of the DNA probe by utilizing the DNA amplification method, PCR (polymerase chain reaction).

1) DNA NAPs Prepared with Analog-Tagged Oligonucleotide Primers

Already developed for use in such a DNA NAP-protection assay is the analog 5-DNP-dU phosphoramidite. This analog can be incorporated chemically into ssDNA oligonucleotides utilizing automated synthesis. Therefore oligonucleotide primers for the PCR reaction can be made which contain multiple analogs, with nearly every "T" in the oligonucleotide synthesis and isolation, and we have shown that it is also retained during the thermal cycling reaction of PCR. Therefore, one can prepare DNA NAPs which contain several reactive thiol groups in the 5' region of the NAP, and these can then be deprotected and modified with a variety of alkylating agents. One can therefore prepare probes for several different mRNA targets, each with a different reporter group, and differentially quantify the levels of each in one reaction. This aspect of the method becomes important for the progression of the assay to automation.

2) DNA NAPs Prepared with Analog-Tagged Deoxynucleoside Triphosphates

DNA NAPs can be synthesized by incorporating several (e.g., five to ten) 5-S-DNP-dUs into the 5'-tagged oligonucleotide, and then synthesizing full length DNA NAP by PCR with unmodified dNTPs, e.g., 5-S-DNP-dUTP.

Automation of NAP Protection Assays

Automation of either the RNA NAP Protection Assay or the DNA NAP Protection Assay requires that the electrophoresis step be eliminated. The separation of the individual protected mRNA species by electrophoresis is one of the more time-consuming steps of the current assay, and makes this method intractable to automation. In order to eliminate this step, one must devise a method for the detection and relative quantitation of more than one mRNA species in a single reaction. Currently, the best approach for this involves the use of a variety of fluorescent tags, each with different excitation and emission properties. An increasing number of alkylating reagents tagged with fluorescent groups such as fluorescein or rhodamine, to name only two of many, are now commercially available. Companies are designing fluorescent detectors which can differentiate among the different signals produced by these fluorescent dyes. This approach is modeled upon the automated assays currently used for nonisotopic DNA sequencing. The final choice of fluorescent dye combinations used for these assays are determined empirically during the course of the first year of this grant. Alternatively, one can label different NAPs with different antigenic groups, so that RNAs could be distinguished with antibodies, a method already utilized in many automated assays.

Deoxyribonuclease NAP Protection Assay

For the DNA NAP assay, one can incorporate commonly used methods for the immobilization of DNA onto resins or microtiter plates. If, for example, a 96-well microtiter plate were coated with streptavidin, then DNA tagged at the 5' end with biotin could be efficiently immobilized. In this way, the DNA NAP and any RNA to which it hybridizes, could be immobilized on a solid matrix, while other components of the hybridization mixture could be washed away.

The following approach can be followed for establishment of an automated DNase NAP Protection Assay.

1) DNA oligonucleotides can be synthesized which are tagged at the 5' end with one of many groups that would allow immobilization of the DNA to a solid matrix (for example biotinylated nucleotides and streptavidin-agarose resin). The DNA NAPs can be multiply-labeled by either:
   a) incorporating several (5–10) 5-S-DNP-dUs into the 5'-tagged oligonucleotide, and then synthesizing full length DNA NAP by PCR with unmodified dNTPs.
   b) incorporating multiple (50–100) 5-S-DNP-dUs into the body of the DNA product produced by PCR by using 5-S-DNP-dUTP as a substrate.

2) The 5' end-labeled, internally reporter-labeled DNA NAPs can be deprotected and modified with one of the reporter groups chosen in the studies described above.

3) Reaction mixtures can be prepared containing multiple mRNA targets and one or more reporter-tagged NAPs.

4) After hybridization, reactions mixtures can be treated with nucleases specific for single-stranded nucleic acids (such as S1 or Hung Bean Nucleases), to produce the protected mRNA species.

5) Reactions mixtures can be added to microtiter plates coated with Streptavidin (for 5'-biotin labeled DNA) or other materials which are specific for binding the groups commonly used to tag DNA probes. Since the 5' end of the DNA is protected during the NAP-protection assay (see FIG. 1), and NAP which does not hybridize are degraded by nuclease, the only material which should bind to the solid matrix is the DNA-mRNA hybrid.

6) Microtiter plates can be washed to remove unincorporated nucleotides, thereby removing essentially all background signal.

7) Plates can be analyzed with a fluorescent microtiter plate reader to quantify the relative amounts of mRNAs produced for different NAPs.

REFERENCES

Agrawal, S., ed. *Methods in Molecular Biology*, ed. Walker, J. M., Vol. 20, Humana Press: Totowa, N.J. (1993).

Barone, A. D., Tang, J.-Y. and Caruthers, M. H. (1984) In situ Activiation of bis-Dialkylaminophosphines—A New Method for Synthesizing Deoxyoligonucleotides on Polymer Supports *Nucleic Acids Res*. 12, 4051–4061.

Bartholomew, B., Braun. F. R., Kassavetis, G. A. and Geiduschek, E. P. (1994) Probing Close DNA Contacts of RNA Polymerase III Transcription Complexes with the Photoactive Nucleoside 4-Thiodeoxythymidine *J. Biol. Chem*. 269, 18090–18095.

Bartholomew, B., Kassavetis. G. A., Braun, B. R. and Geiduschek, E. P. (1990) The Subunit Structure of *Saccharomyces cerevisiae* Transcription Factor IIIC Probed with a Novel Photocrosslinking Reagent *EMBO J*. 9, 2197–2205.

Beaucage, S. L. and Iyer, R. P. (1993) The Functionalization of Oligonucleotides Via Phosphoramidite Derivatives *Tetrahedron* 49, 1925–1963.

Bergstrom, D. E., Beal, P., Jenson, J. and Lin, X. (1991) Palladium-mediated Synthesis of C-5 Pyrimidine Nucleoside Thioethers from Disulfides and Mercurinucleosides *J. Org. Chem*. 56, 5598–5602.

Bleasdale, C., Ellwood, S. B. and Golding, B. T. (1990) 4,4'-Dimethoxytrityl and 4-Monomethoxytrityl Tetrafluoroborate: Convenient Reagents for the Protection of Primary Alcohols Including Sugars *J. Chem. Soc. Perkin Trans* 1 803–804.

Bradley, D. H. and Hanna, M. M. (1992) Synthesis and Utility of 5-Thiocyanato Dexoyuridine and Uridine Phosphoramidites as Masked Synthons *Tetrahedron Lett*. 33, 6223–6226.

Brown, H. C., Narasimhan, S. and Choi, Y. M. (1982) Selective Reduction. 30. Effect of Cation and Solvent on the Reactivity of Saline Borohydrides for Reduction of Carboxylic Esters. Improved Procedures for the Conversion of Esters to Alcohols by Metal Borohydrides *J. Org. Chem*. 47, 4702–4708.

Chaudhary, S. K. and Hernandez, O. (1979) A Simplified Procedure for the Preparation of Triphenylmethyleters *Tetrahedron Lett*. 95–98.

Christopherson, M. S. and Broom, A. D. (1991) Synthesis of Oligonucleotides Containing 2'-Deoxy-6-thioguanosine at a Predetermined Site *Nucleic Acids Res*. 19, 5719–5724.

Clegg, R. M., Murchie, A. I. H., Zechel, A., Carlberg, C., Diekmann, S. and Lilley, D. M. J. (1992) Fluorescence Resonance Energy Transfer Analysis of the Structure of the Four-Way DNA Junction *Biochemistry* 31, 4846–4856.

Clivio, P., Fourrey, J.-L., Gasche, J., Audic, A., Favre, A., Perrin, C.; and Woisard, A. (1992) Synthesis and Purification of Oligonucleotides Containing Sulfur Substituted Nucleobase: 4-Thiouracil, 4-Thiothymine and 6-Mercaptopurine *Tetrahedron Lett*. 33, 65–68.

Coleman, R. S. and Kesicki, E. A. (1994) Synthesis and Postsynthetic Modification of Oligodeoxynucleotides Containing 4-Thio-2'-deoxyuridine ($d^{S4}U$) *J. Am. Chem. Soc*. 116, 11636–11642.

Connolly, B. A. and Newman, P. C. (1989) Synthesis and Properties of Oligonucleotides Containing 4-Thiothymine, 5-Methy-2-pyrimidinone-1-β-D-(2'-deoxyriboside) and 2-Thiothymidine *Nucleic Acids Res*. 17, 4957–4974.

Cosstick, R. and Douglas, M. E. (1991) Synthesis of a Dinucleoside Monophosphate Analogue Containing 6-N-(2-Aminoethyl)-2'-Deoxyadenosine. A Novel Approach to Sequence Specific Crosslinking in Synthetic Oligonucleotides *J. Chem. Soc. Perkin Trans*. 1 1035–1040.

Dissinger, S. and Hanna, M. M., (1990) *J. Biol. Chem*., 265:7662.

Flaschka, H. A., Barnard, A. J. and Sturrock, P. E. (1969) *Quantitative Analytical Chemistry, Short Introduction to Practice*, Barnes & Noble, INC., New York.

Gait, M. J., ed. *Practical Approach Series*, ed. Rickwood, D. and Harnes, B. D., IRL Press: Oxford (1984).

Gao, H., Fathi, R., Gaffney, B. L., Goswami, B., Kung, P.-P., Rhee, Y., Jin, R. and, Jones, R. A. (1992) 6-O-(Pentatluorophenyl)-2'-deoxyguanosine: A Versatile Synthon for Nucleoside and Oligonucleotide Synthesis *J. Org. Chem*. 57, 6954–6959.

Glick, G. D. (1991) Synthesis of a Conformationally Restricted DNA Hairpin *J. Org. Chem*. 56, 6746–6747.

Gibson, K. J. and Benkovic, S. J. (1987) *Nucleic Acid Res*., 15, No. 16:6455.

Goodwin, J. T. and Glick, G. D. (1993) Incorporation of Alkylthiol Chains at C-5 of Deoxyuridine *Tetrahedron Lett*. 34, 5549–5552.

Goodwin, J. T., Osborne, S. E., Swanson, P. C. and Glick, G. D. (1994) Synthesis of a Disulfide Cross-linked DNA Triple Helix *Tetrahedron Lett.* 35, 4527–4530.

Greene, T. W. (1981) *Protective Groups in Organic Synthesis*, John Wiley & Sons, New York.

Grzybowski, J., Will, D. W., Randall, R. E., Smith, C. A. and Brown, T. (1993) Synthesis and Antibody-mediated Detection of Oligonucleotides Containing Multiple 2,4-Dinitrophenyl Reporter Groups *Nucleic Acids Res.* 21, 1705–1712.

Hanna, M. M. (1989) *Methods in Enzymology*, 180:383

Hanna, M. M. (1993) Photocrosslinking Analysis of Protein-RNA Interactions in *E. coli* Transcription Complexes *Cellular Molecular Biology Research* 39, 393–399.

Hanna, M. M., Dissinger, S., Williams, B. D. and Colston, J. E. (1989) Synthesis and Characterization of 5-[4-(Azidophenacyl)thio]uridine 5'-Triphosphate, a Cleavable Photo-Cross-Linking Nucleotide Analogue *Biochemistry* 28, 5814–5820.

He, B. and Hanna, M. M., (1995) *Nucleic Acids Res.*, 23.

Hershey, A. D. and Krause, J. E., (1989) *Science*, 247:960.

Jadhav, V., Barawkar, D., Natu, A., and Ganesh, K. *Nucleosides and Nucleotides*, (1997) 16, 107–114.

Kalman, T. I. and Bardos, T. J. (1967) The Autoxidation of 5-Mercaptouracil and 5-Mercaptodeoxyuridine *J. Am. Chem. Soc.* 89, 1171–1175.

Keller, G. H., and Manak, M. M., (1989) *DNA Probes*, New York, N.Y.: Stockton Press.

Kini, G. D., Robins, R. K. and Avery, T. L. (1989) Synthesis and Antitumor Activity of Ribavirin Imidates. A New Facile Synthesis of Ribavirin Amidine (1-β-D-Ribofuranosyl-1,2,4-triazone-3-carboxamidine Hydrochloride) *J. Med. Chem.* 32, 1447–1449.

Kricka, L. J. (1992) ed. *Nonisotopic DNA Probe Techniques*, Academic Press, Inc.: San Diego, Calif.

Kuimelis, R. G. and Nambiar, K. P. (1994) Synthesis of Oligodeoxynucleotides Containing 2-Thiopyrimidine Residues- A New Protection Scheme *Nucleic Acids Res.* 22, 1429–1436.

Lakshman, M. K., Sayer, J. M., Yagi, H. and Jerina, D. M. (1992) Synthesis and Duplex-Forming Properties of a Nonanucleotide Containing an $N^6$-Deoxyadenosine Adduct of a Bay-Region Diol Epoxide *J. Org. Chem.* 57, 4585–4590.

Maurizi, M. R. and Ginsburg, A. (1986) *Biochemistry*, 25:131.

Mergny, J.-L., Boutorine, A. A., Garestier, T., Belloc, F., Rougee, M., Bulychev, N. V., Koshkin, A. A., Bourson, J., Lebedev, A. V., Valeur, B., Thuong, N. T. and Helene, C. (1994) Fluorescence energy transfer as a probe for nucleic acid structures and sequences *Nucleic Acids Res.* 22, 920,928.

Nagamachi, T., Fourrey, J.-L., Torrence, P. F., Waters, J. A. and Witkop, B. (1974) Synthesis, Chemistry, and Biological Activity of 5-Thiocyanatopyrimidine Nucleosides as Potential Masked Thiols *J. Med. Chem.* 17, 403–406.

Scremin, C. L., Zhou, L., Srinivasachar, K. and Beaucage, S. L. (1994) Stepwise Regeneration and Recovery of Deoxyribonucleoside Phosphoramidite Monomers during Solid-Phase Oligonucleotide Synthesis *J. Org. Chem.* 59, 1963–1966.

Shaltiel, S. (1967) Thiolysis of Some Dinitrophenyl Derivatives of Amino Acids Biochem. *Biophys. Res. Comm.* 29, 178–183.

Sheardy, R. D. and Seeman, N. C. (1986) The Synthesis of a Deoxyoligonucleotide Incorporating 5-Iododeoxyruidine *J. Org. Chem.* 51, 4301–4303.

Sinha, N. D., Biernat, J., McManus, J., and Koster, H. (1984) Polymer Support Oligonucleotide Synthesis XVIII: Use of β-cyanoethyl-N,N-dialkylamino-/N-morpholino Phosphoramidite of Deoxynucleosides for the Synthesis of DNA Fragments Simplifying Deprotection and Isolation of the Final Product *Nucleic Acids Res.* 12, 4539–4557.

Soai, K. and Ookawa, A. (1986) Mixed Solvents Containing Methanol as Useful Reaction Media for Unique Chemoselective Reductions with Lithium Borohydride *J. Org. Chem.* 51, 4000–4005.

Torrence, P. F., Waters, J. A. and Witkop, B. (1968) 2'Deoxy-5'(thiocyanato)uridine [1-(2-deoxy-β-D-erythropentofuranosyl)-5-(thiocyanato)uracil]*Synthetic Procedures in Nucleic Acid Chemistry*, (W. W. Zorbach and R. S. Tipson, Ed.) pp 367–370, Interscience, New York.

Trivedi, B. K. and Bruns, R. F. (1989) C2.$N^6$-Disubstituted Adenosines: Synthesis and Structure-Activity Relationships *J. Med. Chem.* 32, 1667–1673.

Waters, T. R. and Connolly B. A. (1992) Straightforward Synthesis of 6-Thiodeoxyguanosine and Its Incorporation into Oligodeoxynucleotides *Nucleosides Nucleotides* 11, 985–998.

Xu, Y.-Z., Zheng, Q. and Swann, P. F. (1992a) Synthesis and Duplex Stability of Oligodeoxynucleotides Containing 6-Mercaptopurine *Tetrahedron Lett.* 33, 5837–5840.

Xu, Y.-Z., Zheng, Q. and Swann, P. F. (1992b) Synthesis by Post-Synthetic Substitution of Oligomers Containing Guanine Modified at the 6-Position with S-, N-, O-derivatives *Tetrahedron* 48, 1729–1740.

Xu, Y.-Z., Zheng, Q. and Swann, P. F. (1992c) Synthesis of DNA Containing Modified Bases by Postsynthetic Substitution. Synthesis of Oligomers Containing 4-Substituted Thymine: $O^4$-Alkylthymine, 5-Methylcytosine, $N^4$-(Dimethylamino)-5-methylcytosine, and 4-Thiothymine *J. Org. Chem.* 57, 3839–3845.

Yang, X. J., Hart, C. M., Grayhack, E. J. and Roberts, J. W. (1987) Transcription Antitermination by Phage Lambda Gene Q Protein Requires a DNA Segment Spanning the RNA Start Site *Genes Dev* 1, 217–226.

Zhang, Y. and Hanna, M. M. (1995) Expression and Functional Characterization of *Escherichia coli* NusA and Lambda Q as Glutathione-S-Transferase Fusion Proteins *Protein Expression and Purification* 6, 625–631.

Changes may be made in the compounds described herein or in the steps or the sequence of steps of the methods of synthesis or use of the compounds described herein without departing from the spirit and scope of the invention as defined in the following claims.

What is claimed is:

1. A nucleotide analog of the formula:

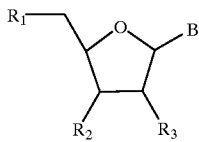

wherein $R_1$ is —H, —OH, a mono, di, or triphosphate group, or —$OR_4$;

$R_2$ is —H, —OH, a mono, di, or triphosphate group, a phosphoramidite group, a phosphorothioamidite group, a phosphonate group, an O-substituted monophosphate group, —$OR_4$, or a solid support bonded via an O at the 3' position;

$R_3$ is —H, —OH, a mono, di, or triphosphate group, or —$OR_4$;

$R_4$ is a lower alkyl or a protecting group; and

B is a modified pyrimidine base comprising a protected thiol group attached at the 5 position on said base that is not involved in Watson-Crick base pairing or does not disrupt normal Watson-Crick base pairing, said protected thiol group selected from the group consisting of a thiodinitrophenyl group, a thioalkyldinitrophenyl group, an alkyldisulfide group, and an -S-phenylacetamidomethyl group; wherein said alkyl is a lower alkyl; and said protected thiol group being stable under conditions of chemical nucleic acid synthesis and/or conditions of enyzmatic nucleic synthesis and being convertible to a reactive thiol after said synthesis.

2. The nucleotide analog of claim 1 wherein said base is selected from the group consisting of cytosine and uracil.

3. The nucleotide analog of claim 1 wherein said base compromises an additional protecting group on a reactive moiety of said base.

4. The nucleotide analog of claim 3 wherein said base is selected from the group consisting of $N^4$-anisoyl cytosine, $N^4$-benzoyl cytosine, $N^4$-isobutyryl cytosine and $N^4$-acetyl cytosine.

5. The nucleotide analog of claim 1 wherein said protected thiol group on said base is selected from the group consisting of thiodinitrophenyl (-SDNP), thioalkyldinitrophenyl (-S-$R_{10}$-DNP), and alkyldisulfide (-S-S-$R_{10}$) wherein $R_{10}$ is a lower alkyl.

6. The nucleotide analog of claim 1, wherein the protecting group of $R_1$ is selected from the group consisting of p-(dimethoxytrityl), p-(monomethoxytrityl), fluorenylmethyloxycarbonyl, levuloyl and 9-phenylxanthene-9-yl.

7. The nucleotide analog of claim 1, wherein protecting group of $R_3$ is selected from the group consisting of 1-(2-chloro-4-methylphenyl)-4-methoxy-4-piperidinium, 2'-acetal, o-nitrobenzyl, tert-butyldimethyl silyl, tetrahydrofuranyl and 4-methoxytetrahydropyranyl.

8. The nucleotide analog of claim 1 wherein $R_1$ is —$OR_4$ wherein $R_4$ is a protecting group and $R_2$ is a phosphoramidite group.

9. The nucleotide analog of claim 8 wherein said base is cytosine, or uracil.

10. The nucleotide analog of claim 9 wherein said base comprises an additional protecting group on a reactive moiety of said base.

11. The nucleotide analog of claim 9 wherein said base is selected from the group consisting of $N^4$-anisoyl cytosine, $N^4$-benzoyl cytosine, $N^4$-isobutyryl cytosine and $N^4$-acetyl cytosine.

12. The nucleotide analog of claim 8 wherein said protected thiol group of said base is selected from the group consisting of thiodinitrophenyl (-SDNP), thioalkyldinitrophenyl (-S-$R_{10}$-DNP), and alkyldisulfide (-S-S-$R_{10}$) wherein $R_{10}$ is a lower alkyl.

13. The nucleotide analog of claim 8 wherein the protecting group of $R_1$ is selected from the group consisting of p-(dimethoxytrityl), p-(monomethoxytrityl), fluorenylmethyloxycarbonyl, levuloyl, and 9-phenylxanthene-9-yl.

14. The nucleotide analog of claim 8, wherein the protecting group of $R_3$ is selected from the group consisting of 1-(2-chloro- 4-methylphenyl)-4-methoxy-4-piperidinyl, 2'-acetal, o-nitrobenzyl, tert-butyldimethyl silyl, tetrahydrofuranyl and 4-methoxytetrahydropyranyl.

15. The nucleotide analog of claim 1 or 8, wherein said phosphoramidite of $R_2$ is represented by the formula:

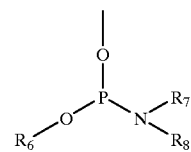

$R_6$ is a lower alkyl, cyanoethyl or a substituted lower alkyl; and $R_7$ and $R_8$ are independently lower alkyls, or when taken together with the nitrogen to which they are attached comprise one of the groups:

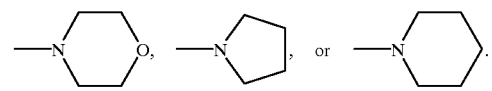

16. The nucleotide analog of claim 1 wherein $R_1$ is —$OR_4$ wherein $R_4$ is a protecting group and $R_2$ is a phosphorothioamidite group.

17. The nucleotide analog of claim 1 or 16, wherein said $R_2$ is a phosphorothioamidite represented by the formula:

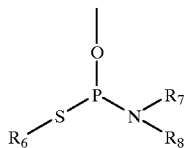

wherein

R$_6$ is a lower alkyl, cyanoethyl or a substituted lower alkyl; and

R$_7$ and R$_8$ are independently lower alkyls, or when taken together with the nitrogen to which they are attached comprise one of the groups:

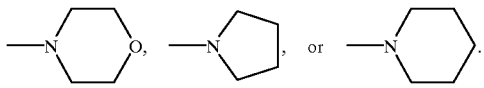

18. The nucleotide analog of claim 1 wherein R$_2$ is an O-substituted monophosphate group selected from the group consisting of -2-chlorophenyl monophosphate, O-2,5-dichlorophenyl monophosphate, O-2,2,2-trichloroethyl monophosphate and the N oxide of 4-methoxypyridine-2-methylene monophosphate.

19. A nucleotide analog of the formula:

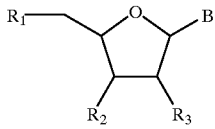

wherein

R$_1$ is —H, —OH, a mono, di, or triphosphate group, or —OR$_4$;

R$_2$ is a phosphoramidite group;

R$_3$ is —H, —OH, a mono, di, or triphosphate group, or —OR$_4$;

R$_4$ is a lower alkyl or a protecting group; and

B is a modified pyrimidine base comprising a protected thiol group attached at the 5 position on said pyrimidine base, said protected thiol group selected from the group consisting of a thiodinitrophenyl group, a thioalkyldinitrophenyl group, an alkyldisulfide group, and a -S-phenylacetamidomethyl group; wherein said alkyl is a lower alkyl.

20. The nucleotide analog of claim 19 wherein said base is selected from the group consisting of N$^4$-anisoyl cytosine, N$^4$-benzoyl cytosine, N$^4$-isobutyryl cytosine and N$^4$-acetyl cytosine.

21. The nucleotide analog of claim 19, wherein R$_1$ is —OR$_4$ and R$_4$ is a protecting group selected from the group consisting of p-(dimethoxytrityl), p-(monomethoxytrityl), fluorenylmethyloxycarbonyl, levuloyl, and 9-phenylxanthene-9-yl.

22. The nucleotide analog of claim 19 wherein said phosphoramidite of R$_2$ is represented by the formula:

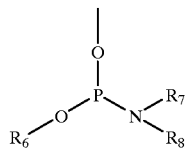

wherein

R$_6$ is a lower alkyl, cyanoethyl or substituted lower alkyl; and

R$_7$ and R$_8$ are independently lower alkyls, or when taken together with the nitrogen to which they are attached form the groups:

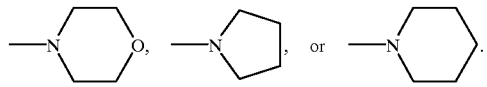

23. The nucleotide analog of claim 22 wherein R$_6$ is 2-cyanoethyl, R$_7$ is isopropyl and R$_8$ is isopropyl.

24. The nucleotide analog of claim 23 wherein said base is uridine or deoxyuridine.

25. The nucleotide analog of claim 24 wherein R$_1$ is —OR$_4$ and R$_4$ is p-(dimethoxytrityl).

26. A nucleotide analog of the formula:

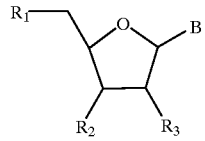

wherein:

R$_1$ is —H, —OH, a mono, di, or triphosphate group, or —OR$_4$;

R$_2$ is —H, —OH, a mono, di, or triphosphate group, a phosphoramidite group, a phosphorothioamidite group, a phosphonate group, an O-substituted monophosphate group, —OR$_4$, or a solid support bonded via an O at the 3' position;

R$_3$ is —H, —OH, a mono, di, or triphosphate group, or —OR$_4$;

R$_4$ is a lower alkyl or a protecting group; and

B is a modified pyrimidine base comprising a protected thiol group attached at the 5 position on said base, said protected thiol group selected from the group consisting of a thiodinitrophenyl group, a thioalkyldinitrophenyl group, an alkyldisulfide group, and a -S-phenylacetamidomethyl group; wherein said alkyl is a lower alkyl.

27. The nucleotide analog of claim 26 wherein said base is cytosine, or uracil.

28. The nucleotide analog of claim 26 wherein said protected thiol group on said base is selected from the group consisting of thiodinitrophenyl (-SDNP), thioalkyldinitrophenyl (-S-R$_{10}$-DNP), S-phenylacetamidomethyl(-S-CH$_2$NHCOCH$_2$Ph) wherein R$_{10}$ is a lower alkyl.

29. The nucleotide analog of claim 26, wherein R$_1$ is a monophosphate, a diphosphate, or a triphosphate.

30. An oligonucleotide containing the incorporated form of the nucleotide analog of any one of claims 1, 8, 16, 19, or 26.

31. A method of producing the nucleotide analog of any one of claims 1, 8, 16, 19, or 26 which comprises preparing the thiol-protected nucleoside or nucleotide base wherein said thiol is attached to the 5 position on said base; reacting said nucleoside or nucleotide base under conditions to effect conversion of said base to a phosphoramidite, phosphorothioamidite, phosphonate, O-substituted monophosphate or phosphate nucleotide analog and under conditions which do not destroy the protected thiol; and recovering said analog.

32. A method of synthesizing a nucleic acid having an attached functional group which comprises incorporating a thiol-protected nucleotide analog of any one of claims 1, 8, 16, 19, or 26 into a nucleic acid by a chemical or enzymatic method of nuicleic acid synthesis; recovering said nucleic acid containing said analog; deprotecting the analog of said nucleic acid to produce a nucleic acid containing a reactive thiol group; treating the reactive thiol group with a thiol modifying reagent to thereby attach a functional group and produce said nucleic acid with an attached functional group; and recovering said nucleic acid with said attached functional group.

33. The method of claim 32 wherein said functional group is selected from the group consisting of a photocrosslinker, a crosslinker, a reporter molecule, a radioisotope, a fluorescent group, a spin label, chemiluminescent or an antigenic group.

34. The method of claim 33 wherein said photocrosslinker is an aryl azide.

35. The method of claim 33 wherein said reporter group is biotin, an enzyme, or a fluorescent molecule.

36. The method of claim 33 wherein said fluorescent group is fluorescein.

37. A method for producing a deoxyuridine analog having a protected thiol group on the 5 position, comprising:

reacting a diacetyl 5-thiocyanate deoxyuridine to form a 5-dinitrophenylthio deoxyuridine;

converting said 5-dinitrophenylthio deoxyuridine to a phosphoramidite, phosphorothioamidite, phosphonate, O-substituted monophosphate or phosphate nucleotide analog under conditions which do not destroy the 5-dinitrophenylthio group;

and recovering said 5-dinitrophenylthio deoxyuridine analog.

* * * * *

UNITED STATES PATENT AND TRADEMARK OFFICE
CERTIFICATE OF CORRECTION

PATENT NO. : 6,008,334
DATED : December 28, 1999
INVENTOR(S) : Michelle M. Hanna It is certified that error appears in the above-identified patent and that said Letters Patent is hereby corrected as shown below:

Item [57] Abstract,
Line 6, delete "as well a" and substitute therefor -- as well as --;

Column 4,
Line 63, delete "oligonucleotides" and substitute therefor -- Oligonucleotides --;

Column 5,
Line 19, delete "oligonucleotide" and substitute therefor -- Oligonucleotide --;

Column 8,
Line 55, delete "gtianine-cytosine" and substitute therefor -- quanine-cytosine --;

Column 19,
Line 61, delete "Thibcyanation" and substitute therefor -- Thiocyanation --;

Column 20,
Line 65, delete "NaOMe;" and substitute -- NaOMe, -- therefor;

Column 23,
Line 43, delete "DXT" and substitute therefor -- DMT --;

Column 29,
Line 23, delete "krause," and substitute -- Krause, -- therefor;

Column 31,
Line 5, delete "are";

Column 33,
Line 29, delete "Hung" and substitute -- Mung -- therefor;

UNITED STATES PATENT AND TRADEMARK OFFICE
CERTIFICATE OF CORRECTION

PATENT NO. : 6,008,334
DATED : December 28, 1999
INVENTOR(S) : Michelle M. Hanna It is certified that error appears in the above-identified patent and that said Letters Patent is hereby corrected as shown below:

Column 34,
Line 19, delete "Triphenylmethyleters" and substitute -- Triphenylmethylethers -- therefor;
Line 58, delete "(Pentatluorophenyl)-" and substitute -- (Pentafluorophenyl)- -- therefor; and Column 39,
Line 47 (line 2 of claim 3), delete "compromises" and substitute -- comprises -- therefor.

Signed and Sealed this

Sixth Day of November, 2001

Attest:

*Attesting Officer*

NICHOLAS P. GODICI
*Acting Director of the United States Patent and Trademark Office*

SEQUENCE LISTING

<160> NUMBER OF SEQ ID NOS: 6

<210> SEQ ID NO 1
<211> LENGTH: 24 base pairs
<212> TYPE: DNA
<213> ORGANISM: Artificial Sequence
<220> FEATURE:
<223> OTHER INFORMATION: completely synthesized

<400> SEQUENCE: 1 cgc gga att ctc atg cat tgc cca                24

<210> SEQ ID NO 2
<211> LENGTH: 20 base pairs
<212> TYPE: DNA
<213> ORGANISM: Artificial Sequence
<220> FEATURE:
<223> OTHER INFORMATION: completely synthesized

<400> SEQUENCE: 2 aa att tga ctc aac gat ggg                     20

<210> SEQ ID NO 3
<211> LENGTH: 22 base pairs
<212> TYPE: DNA
<213> ORGANISM: Artificial Sequence
<220> FEATURE:
<223> OTHER INFORMATION: completely synthesized

<400> SEQUENCE: 3 gac tca acg atg ggt taa ttc g                  22

<210> SEQ ID NO 4
<211> LENGTH: 22 base pairs
<212> TYPE: DNA
<213> ORGANISM: Artificial Sequence
<220> FEATURE:
<223> OTHER INFORMATION: completely synthesized
<220> FEATURE:
<221> NAME/KEY: modified base
<222> LOCATION: position 11
<223> OTHER INFORMATION: n represents a pyrimidine base having a modified thiol group
      at the 5 position on the base

<400> SEQUENCE: 4 gac tca acg ang ggt taa ttc g                  22

<210> SEQ ID NO 5
<211> LENGTH: 24 base pairs
<212> TYPE: DNA
<213> ORGANISM: Artificial Sequence
<220> FEATURE:
<223> OTHER INFORMATION: completely synthesized

<400> SEQUENCE: 5 ggg taa att tga ctc aac gat ggg                24

<210> SEQ ID NO 6
<211> LENGTH: 24 base pairs
<212> TYPE: DNA
<213> ORGANISM: Artificial Sequence
<220> FEATURE:
<223> OTHER INFORMATION: completely synthesized
<220> FEATURE:
<221> NAME/KEY: modified base
<222> LOCATION: position 4
<223> OTHER INFORMATION: n represents a pyrimidine base having a modified thiol group -continued

```
     at the 5 position on the base

<400> SEQUENCE: 6 ggg naa att tga ctc aac gat ggg                        24
```